US012594074B2

(12) United States Patent

Shelton, IV et al.

(10) Patent No.: US 12,594,074 B2

(45) Date of Patent: Apr. 7, 2026

(54) STAPLE CARTRIDGE COMPRISING WALL STRUCTURES TO REDUCE CARTRIDGE DEFLECTION

(71) Applicant: Cilag GmbH International, Zug (CH)

(72) Inventors: Frederick E. Shelton, IV, Hillsboro, OH (US); Adam D. Hensel, Gahanna, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/379,801

(22) Filed: Oct. 13, 2023

(65) Prior Publication Data

US 2025/0120702 A1 Apr. 17, 2025

(51) Int. Cl.
*A61B 17/072* (2006.01)

(52) U.S. Cl.
CPC .. *A61B 17/072* (2013.01); *A61B 2017/07228* (2013.01); *A61B 2017/0725* (2013.01); *A61B 2017/07271* (2013.01); *A61B 2017/07278* (2013.01); *A61B 2017/07285* (2013.01)

(58) Field of Classification Search
CPC .......... A61B 17/072; A61B 2017/0725; A61B 2017/07271; A61B 2017/07278; A61B 2017/07285
USPC ........................................... 227/175.1–182.1
See application file for complete search history.

(56) References Cited

U.S. PATENT DOCUMENTS 5,403,312 A    4/1995  Yates et al.
5,485,947 A    1/1996  Olson et al.

6,978,921 B2    12/2005  Shelton, IV et al.
7,000,818 B2 *   2/2006  Shelton, IV  ..... A61B 17/07207
                                                  227/176.1
7,401,721 B2    7/2008  Holsten et al.
7,407,075 B2    8/2008  Holsten et al.
7,422,139 B2    9/2008  Shelton, IV et al.
(Continued)

FOREIGN PATENT DOCUMENTS

CN          105919642 A      9/2016
CN          105997172 A     10/2016
(Continued)

OTHER PUBLICATIONS

U.S. Appl. No. 12/031,573, filed Feb. 14, 2008.
(Continued)

*Primary Examiner* — Robert F Long
*Assistant Examiner* — Xavier A Madison
(74) *Attorney, Agent, or Firm* — Lempia Summerfield Katz LLC

(57) ABSTRACT

A surgical stapling assembly comprising a cartridge body, a plurality of staples, a plurality of staple drivers, a sled, and a support plane is disclosed. The cartridge body comprises a deck, a plurality of staple cavities defined in the deck, a longitudinal slot defined in the deck, and an outer cartridge wall. The support plane extends perpendicular to a longitudinal axis, wherein the sled is positioned under an inner cartridge wall in the support plane, wherein the inner cartridge wall comprises a first lateral pillar width and a first pillar height in the support plane, wherein the outer cartridge wall comprises a second lateral pillar width and a second pillar height in the support plane, and wherein the first lateral pillar width is wider than the second lateral pillar width.

18 Claims, 6 Drawing Sheets

(56) References Cited

U.S. PATENT DOCUMENTS

| | | | |
|---|---|---|---|
| 7,464,849 | B2 | 12/2008 | Shelton, IV et al. |
| 7,669,746 | B2 | 3/2010 | Shelton, IV |
| 7,670,334 | B2 | 3/2010 | Hueil et al. |
| 7,735,703 | B2 | 6/2010 | Morgan et al. |
| 7,753,245 | B2 | 7/2010 | Boudreaux et al. |
| 7,845,537 | B2 | 12/2010 | Shelton, IV et al. |
| 7,980,443 | B2 | 7/2011 | Scheib et al. |
| 8,123,100 | B2 | 2/2012 | Holsten et al. |
| 8,141,762 | B2 | 3/2012 | Bedi et al. |
| 8,210,411 | B2 | 7/2012 | Yates et al. |
| 8,220,688 | B2 | 7/2012 | Laurent et al. |
| 8,308,040 | B2 | 11/2012 | Huang et al. |
| 8,393,514 | B2 | 3/2013 | Shelton, IV et al. |
| 8,499,992 | B2 | 8/2013 | Whitman et al. |
| 8,540,133 | B2 | 9/2013 | Bedi et al. |
| 8,561,870 | B2 | 10/2013 | Baxter, III et al. |
| 8,608,045 | B2 | 12/2013 | Smith et al. |
| 8,733,613 | B2 | 5/2014 | Huitema et al. |
| 8,864,007 | B2 | 10/2014 | Widenhouse et al. |
| 8,876,857 | B2 | 11/2014 | Burbank |
| 8,899,464 | B2 | 12/2014 | Hueil et al. |
| 9,050,083 | B2 | 6/2015 | Yates et al. |
| 9,072,535 | B2 | 7/2015 | Shelton, IV et al. |
| 9,101,358 | B2 | 8/2015 | Kerr et al. |
| 9,131,940 | B2 | 9/2015 | Huitema et al. |
| 9,345,481 | B2 | 5/2016 | Hall et al. |
| 9,386,988 | B2 | 7/2016 | Baxter, III et al. |
| 9,629,631 | B2 | 4/2017 | Nicholas et al. |
| 9,770,245 | B2 | 9/2017 | Swayze et al. |
| 9,788,835 | B2 | 10/2017 | Morgan et al. |
| 9,839,420 | B2 | 12/2017 | Shelton, IV et al. |
| 9,844,369 | B2 | 12/2017 | Huitema et al. |
| 9,844,376 | B2 | 12/2017 | Baxter, III et al. |
| 9,924,944 | B2 | 3/2018 | Shelton, IV et al. |
| 9,987,008 | B2 | 6/2018 | Scirica et al. |
| 10,080,552 | B2 | 9/2018 | Nicholas et al. |
| 10,085,749 | B2 | 10/2018 | Cappola et al. |
| 10,105,142 | B2 | 10/2018 | Baxter, III et al. |
| 10,123,798 | B2 | 11/2018 | Baxter, III et al. |
| 10,130,363 | B2 | 11/2018 | Huitema et al. |
| 10,166,023 | B2 | 1/2019 | Vendely et al. |
| 10,213,203 | B2 | 2/2019 | Swayze et al. |
| 10,299,792 | B2 | 5/2019 | Huitema et al. |
| 10,349,939 | B2 | 7/2019 | Shelton, IV et al. |
| 10,357,252 | B2 | 7/2019 | Harris et al. |
| 10,517,593 | B2 | 12/2019 | Gupta et al. |
| 10,537,324 | B2 | 1/2020 | Shelton, IV et al. |
| 10,542,981 | B2 | 1/2020 | Miller et al. |
| 10,561,419 | B2 | 2/2020 | Beardsley |
| 10,568,624 | B2 | 2/2020 | Shelton, IV et al. |
| 10,588,623 | B2 | 3/2020 | Schmid et al. |
| 10,765,427 | B2 | 9/2020 | Shelton, IV et al. |
| 10,898,183 | B2 | 1/2021 | Shelton, IV et al. |
| 10,898,191 | B2 | 1/2021 | Huitema et al. |
| 10,945,727 | B2 | 3/2021 | Shelton, IV et al. |
| 10,952,724 | B2 | 3/2021 | Shelton, IV et al. |
| 11,000,278 | B2 | 5/2021 | Shelton, IV et al. |
| 11,045,191 | B2 | 6/2021 | Shelton, IV et al. |
| 11,058,426 | B2 | 7/2021 | Nalagatla et al. |
| D933,220 | S | 10/2021 | Tate et al. |
| 11,147,552 | B2 | 10/2021 | Burbank et al. |
| 11,207,065 | B2 | 12/2021 | Harris et al. |
| 11,229,433 | B2 | 1/2022 | Schings et al. |
| 11,234,698 | B2 | 2/2022 | Shelton, Iv et al. |
| 11,234,700 | B2 | 2/2022 | Ragosta et al. |
| 11,291,445 | B2 | 4/2022 | Shelton, IV et al. |
| 11,298,129 | B2 | 4/2022 | Bakos et al. |
| 11,337,693 | B2 | 5/2022 | Hess et al. |
| 11,364,029 | B2 | 6/2022 | Burbank et al. |
| 11,382,627 | B2 | 7/2022 | Huitema et al. |
| D967,421 | S | 10/2022 | Shelton, IV et al. |
| 11,490,890 | B2 | 11/2022 | Harris et al. |
| 11,517,315 | B2 | 12/2022 | Huitema et al. |
| D974,560 | S | 1/2023 | Shelton, IV et al. |
| 11,540,826 | B2 | 1/2023 | Nalagatla et al. |
| 11,571,213 | B2 | 2/2023 | Huitema et al. |
| 11,589,865 | B2 | 2/2023 | Shelton, IV et al. |
| 11,701,114 | B2 | 7/2023 | Shelton, IV et al. |
| 11,737,752 | B2 | 8/2023 | Schings et al. |
| 11,766,257 | B2 | 9/2023 | Shelton, IV et al. |
| 11,826,047 | B2 | 11/2023 | Huang et al. |
| 11,849,944 | B2 | 12/2023 | Shelton, IV et al. |
| 11,849,947 | B2 | 12/2023 | Giordano et al. |
| 11,896,218 | B2 | 2/2024 | Bakos et al. |
| 11,974,741 | B2 | 5/2024 | Moubarak et al. |
| 2007/0175955 | A1 | 8/2007 | Shelton et al. |
| 2014/0001231 | A1 | 1/2014 | Shelton, IV et al. |
| 2014/0263552 | A1 | 9/2014 | Hall et al. |
| 2015/0108198 | A1 | 4/2015 | Estrella |
| 2015/0134077 | A1 | 5/2015 | Shelton, IV et al. |
| 2018/0132849 | A1 | 5/2018 | Miller et al. |
| 2018/0168615 | A1 | 6/2018 | Shelton, IV et al. |
| 2019/0105047 | A1 | 4/2019 | Nalagatla et al. |
| 2020/0305867 | A1 | 10/2020 | Switalski et al. |
| 2022/0031320 | A1 | 2/2022 | Hall et al. |
| 2022/0047265 | A1 | 2/2022 | Miller et al. |
| 2022/0304679 | A1 * | 9/2022 | Bakos ................... B33Y 80/00 |
| 2022/0346858 | A1 | 11/2022 | Aronhalt et al. |
| 2023/0119119 | A1 | 4/2023 | Moubarak |

FOREIGN PATENT DOCUMENTS

| | | | |
|---|---|---|---|
| CN | 105997173 | A | 10/2016 |
| CN | 106036848 | A | 10/2016 |
| CN | 108542454 | A | 9/2018 |
| CN | 111195142 | A | 5/2020 |

OTHER PUBLICATIONS

U.S. Food and Drug Administration 510(k) Premarket Notification, https://www.accessdata.fda.cov/scripts/cdrh/cfdocs/cfpmn/pmn.cfm?ID=K182476, last update: Jan. 8, 2024, 1 page.

* cited by examiner

STAPLE CARTRIDGE COMPRISING WALL STRUCTURES TO REDUCE CARTRIDGE DEFLECTION

BACKGROUND

The present invention relates to surgical instruments and, in various arrangements, to surgical stapling and cutting instruments and staple cartridges for use therewith that are designed to staple and cut tissue.

SUMMARY

A surgical stapling assembly comprising a cartridge body, a plurality of staples, a plurality of staple drivers, a sled, and a support plane is disclosed. The cartridge body comprises a deck configured to support patient tissue, wherein the deck comprises a proximal end and a distal end, a plurality of staple cavities defined in the deck, a longitudinal slot defined in the deck, wherein the longitudinal slot extends from the proximal end toward the distal end, wherein the longitudinal slot defines a longitudinal axis, wherein the longitudinal slot is defined by an inner cartridge wall, wherein the staple cavities are arranged in longitudinal rows on opposite sides of the longitudinal slot, and wherein the longitudinal slot is configured to receive at least a portion of a firing driver during a firing stroke, and an outer cartridge wall extending longitudinally between the proximal end and the distal end. The plurality of staples are removably stored in the staple cavities. The sled is movable longitudinally through the cartridge body from a proximal unfired position to a distal fired position by the firing driver to lift the staple drivers within the staple cavities to eject the staples from the staple cavities during the firing stroke. The support plane extends perpendicular to the longitudinal axis, wherein the sled is positioned under the inner cartridge wall in the support plane, wherein the inner cartridge wall comprises a first lateral pillar width and a first pillar height in the support plane, wherein the first lateral pillar width comprises an average lateral width of the inner cartridge wall along the first pillar height, wherein the outer cartridge wall comprises a second lateral pillar width and a second pillar height in the support plane, wherein the second lateral pillar width comprises an average lateral width of the outer cartridge wall along the second pillar height, and wherein the first lateral pillar width is wider than the second lateral pillar width.

LISTING OF THE FIGURES

Various features of the embodiments described herein, together with advantages thereof, may be understood in accordance with the following description taken in conjunction with the accompanying drawings as follows.

Corresponding reference characters indicate corresponding parts throughout the several views.

DETAILED DESCRIPTION

Figure 1:
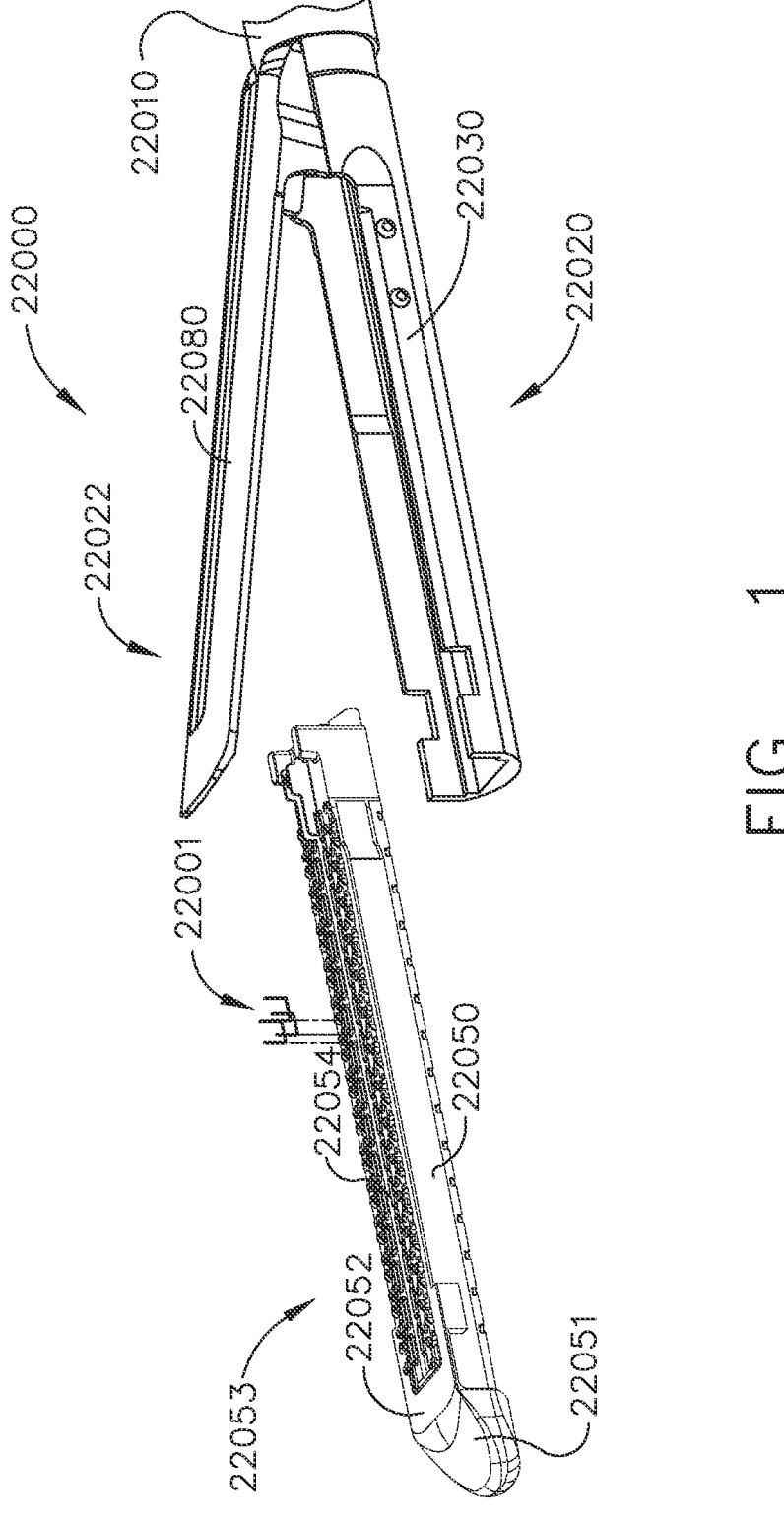
FIG. 1 is a perspective view of a surgical stapling assembly comprising a shaft, a cartridge channel jaw configured to receive a staple cartridge assembly therein, and an anvil jaw in accordance with the present disclosure.

Applicant of the present application owns the following U.S. Patent Applications that were filed on Oct. 13, 2023 and which are each herein incorporated by reference in their respective entireties:

U.S. patent application Ser. No. 18/379,759, titled METHOD OF OPERATING A SURGICAL STAPLING INSTRUMENT;

U.S. patent application Ser. No. 18/379,762, titled SURGICAL STAPLING SYSTEMS WITH ADAPTIVE STAPLE FIRING ALGORITHMS;

U.S. patent application Ser. No. 18/379,763, titled LEARNED TRIGGERS FOR ADAPTIVE CONTROL OF SURGICAL STAPLING SYSTEMS;

U.S. patent application Ser. No. 18/379,766, titled CONTROL CIRCUIT FOR ACTUATING MOTORIZED FUNCTION OF SURGICAL STAPLING INSTRUMENT UTILIZING INERTIAL DRIVE TRAIN PROPERTIES;

U.S. patent application Ser. No. 18/379,768, titled PROPORTIONATE BALANCING OF THE FUNCTION IMPACT MAGNITUDE OF BATTERY OUTPUT TO PEAK MOTOR CURRENT;

U.S. patent application Ser. No. 18/379,771, titled MOTOR OPTIMIZATION BY MINIMIZATION OF PARASITIC LOSSES AND TUNING MOTOR DRIVE CONFIGURATION;

U.S. patent application Ser. No. 18/379,773, titled APPARATUS AND METHOD TO REDUCE PARASITIC LOSSES OF THE ELECTRICAL SYSTEM OF A SURGICAL INSTRUMENT;

U.S. patent application Ser. No. 18/379,776, titled SURGICAL TOOL WITH RELAXED FLEX CIRCUIT ARTICULATION;

U.S. patent application Ser. No. 18/379,777, titled WIRING HARNESS FOR SMART STAPLER WITH MULTI AXIS ARTICULATION;

U.S. patent application Ser. No. 18/379,781, titled SURGICAL SYSTEM WITH WIRELESS ARRAY FOR POWER AND DATA TRANSFER;

U.S. patent application Ser. No. 18/379,784, titled SURGICAL STAPLE CARTRIDGE COMPRISING REPLACEABLE ELECTRONICS PACKAGE;

Applicant of the present application owns the following U.S. Patent Applications that were filed on Oct. 13, 2023 and which are each herein incorporated by reference in their respective entireties:

U.S. patent application Ser. No. 18/379,790, titled METHOD OF ASSEMBLING A STAPLE CARTRIDGE;

U.S. patent application Ser. No. 18/379,793, titled CONTROL SURFACES ON A STAPLE DRIVER OF A SURGICAL STAPLE CARTRIDGE;

U.S. patent application Ser. No. 18/379,793, titled INTEGRAL CARTRIDGE STIFFENING FEATURES TO REDUCE CARTRIDGE DEFLECTION;

U.S. patent application Ser. No. 18/379,803, titled PANLESS STAPLE CARTRIDGE ASSEMBLY COMPRISING RETENTION FEATURES FOR HOLDING STAPLE DRIVERS AND SLED;

U.S. patent application Ser. No. 18/379,805, titled STAPLE CARTRIDGE COMPRISING A SLED HAVING A DRIVER LIFT CAM;

U.S. patent application Ser. No. 18/379,808, titled SURGICAL STAPLE CARTRIDGES WITH SLEDS CONFIGURED TO BE COUPLED TO A FIRING DRIVER OF A COMPATIBLE SURGICAL STAPLER;

U.S. patent application Ser. No. 18/379,810, titled STAPLE CARTRIDGE COMPRISING A COMPOSITE SLED;

U.S. patent application Ser. No. 18/379,811, titled SURGICAL INSTRUMENTS WITH JAW AND FIRING ACTUATOR LOCKOUT ARRANGEMENTS LOCATED PROXIMAL TO A JAW PIVOT LOCATION;

U.S. patent application Ser. No. 18/379,815, titled SURGICAL INSTRUMENTS WITH LATERALLY ENGAGEABLE LOCKING ARRANGEMENTS FOR LOCKING A FIRING ACTUATOR;

U.S. patent application Ser. No. 18/379,817, titled DUAL INDEPENDENT KEYED LOCKING MEMBERS ACTING ON THE SAME DRIVE MEMBER;

U.S. patent application Ser. No. 18/379,820, titled ADJUNCTS FOR USE WITH SURGICAL STAPLING INSTRUMENTS;

U.S. patent application Ser. No. 18/379,822, titled ADJUNCTS FOR USE WITH SURGICAL STAPLING INSTRUMENTS;

U.S. patent application Ser. No. 18/379,826, titled JAW CONTROL SURFACES ON A SURGICAL INSTRUMENT JAW;

U.S. patent application Ser. No. 18/379,827, titled ZONED ALGORITHM ADAPTIVE CHANGES BASED ON CORRELATION OF COOPERATIVE COMPRESSION CONTRIBUTIONS OF TISSUE;

U.S. patent application Ser. No. 18/379,831, titled STAPLE CARTRIDGES COMPRISING TRACE RETENTION FEATURES;

U.S. patent application Ser. No. 18/379,832, titled STAPLE CARTRIDGES COMPRISING STAPLE RETENTION FEATURES;

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

The staple cartridge of a surgical stapling end effector can be particularly vulnerable, or susceptible, to bending—elastically and/or plastically—when subjected to a compressive load. This vulnerability can be attributed, at least in part, to the materials comprising the staple cartridge as compared to the materials comprising a cartridge channel jaw—within which a staple cartridge is positioned—and/or a jaw positioned opposite the staple cartridge such as, for example, an anvil jaw. The staple cartridge can be comprised of a plastic material while the cartridge channel jaw and the anvil jaw are comprised of a metal material, such as stainless steel, for example, and, because of the different elasticity, flexibility, and strength characteristics of such materials, the staple cartridge may tend to elastically deflect, and/or twist, from its original shape under certain loads, such as compressive loads, for example.

This vulnerability of the staple cartridge can also be attributed to the nature of how the components of surgical stapling end effectors fit together. More specifically, some surgical stapling end effectors can include a longitudinally translatable cutting member that traverses a longitudinal slot defined in the staple cartridge to cut tissue clamped between the jaws. The longitudinal slot can increase how much the staple cartridge and/or portions of the staple cartridge can twist or deflect from its original shape under load. Some surgical stapling end effectors also include a translatable sled comprising ramped wedges configured to eject staples from the staple cartridge during the staple firing stroke. The sled can comprise a base which requires space to translate through the surgical stapling end effector. This space, often times positioned between a cartridge body and a pan attached to the cartridge body, defines a void or cavity into which portions of the staple cartridge can deflect. If a pan is not attached to the cartridge body, a similar void or cavity is present between the cartridge body and the cartridge channel jaw.

Staple cartridges can be prone to collapsing when subjected to loads. A staple cartridge collapses when the two opposing sides of the longitudinal slot extending within the staple cartridge rotate or bend inwardly. Forces capable of collapsing a staple cartridge can occur when patient tissue is clamped against the staple cartridge and/or when staples are fired from the staple cartridge during a staple firing stroke. Initial clamping forces can be applied to the staple cartridge when the jaws are approximated to clamp tissue therebetween or, in other words, during a clamping stroke. A firing driver, such as an I-beam, for example, can engage the cartridge channel jaw and the anvil jaw of a surgical stapling assembly during the firing stroke which creates a compressive load against the deck of the staple cartridge. The location of the I-beam can represent the location at which the staple cartridge may be most prone to collapsing.

The deflection of a staple cartridge can cause the staples being ejected from the staple cartridge to be misaligned with their corresponding anvil forming pockets. Such deflection may also cause tissue to bunch up near the longitudinal slot which can increase the difficulty of cutting the tissue during the staple firing stroke. Such deflection can also cause binding between various components of the surgical stapling assembly such as, for example, the staple drivers and staple cavities of the staple cartridge, the I-beam and the longitudinal slot of the staple cartridge, and/or the sled and the cartridge body of the staple cartridge, among others. Binding between such components can cause the components to jam and/or increase the required force to staple and cut tissue, for example.

Figure 2:
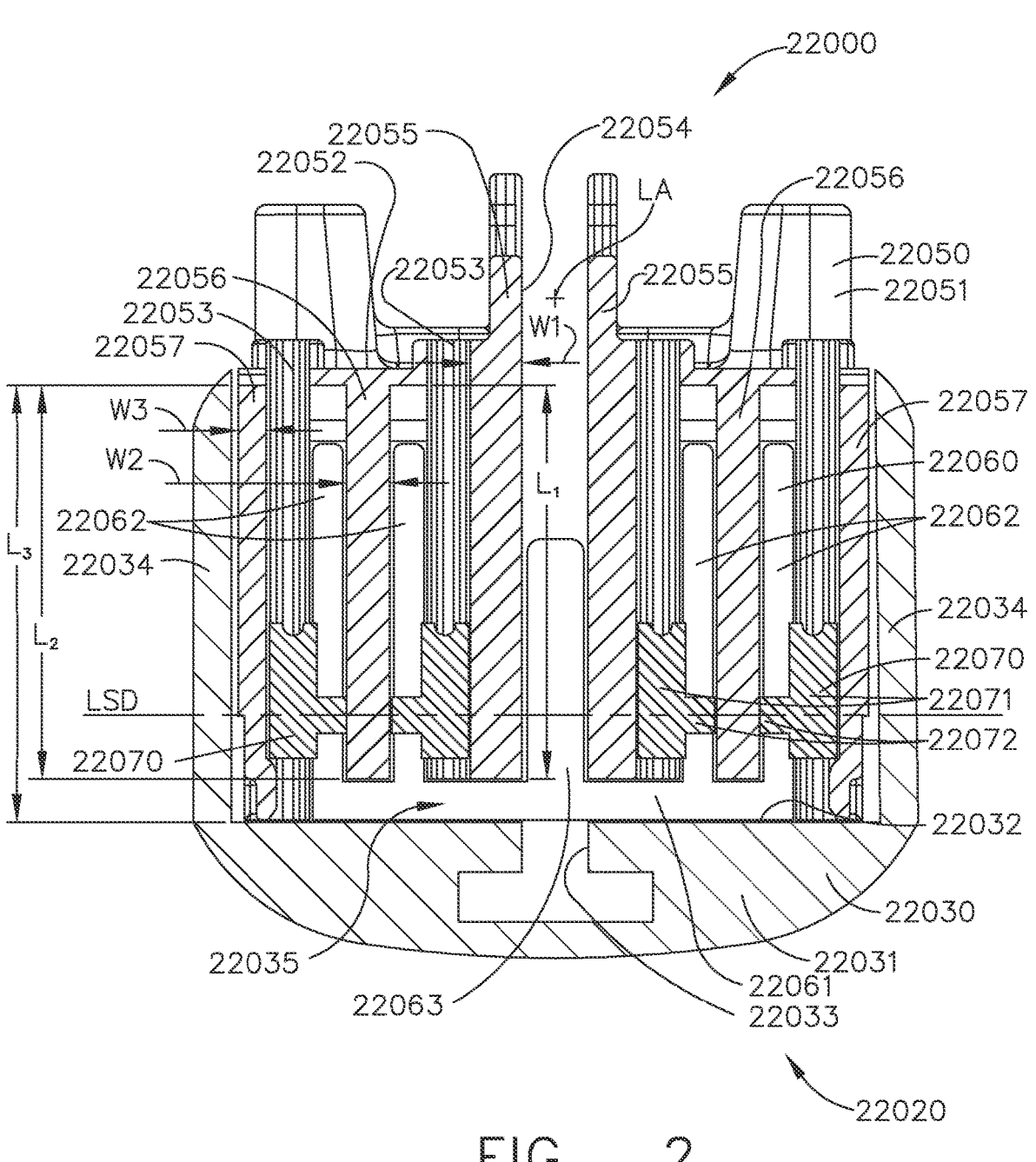
FIG. 2 is a cross-sectional view of the surgical stapling assembly of FIG. 1 illustrating inner cartridge walls, intermediate cartridge walls, and outer cartridge walls of a staple cartridge seated in the cartridge channel jaw.

FIGS. 1 and 2 depict a surgical stapling assembly 22000 that is configured to clamp, staple, and cut patient tissue. The surgical stapling assembly 22000 comprises a shaft 22010, a cartridge channel jaw 22020, and an anvil jaw 22022 movable relative to the cartridge channel jaw 22020 to clamp tissue between the anvil jaw 22022 and a staple cartridge assembly 22050 positioned in the cartridge channel jaw 22020. The staple cartridge assembly 22050 is replaceable and is configured to be readily installed in, and removed from, the cartridge channel jaw 22020 during a surgical procedure; however, a cartridge channel jaw may comprise a staple cartridge assembly therein that is not replaceable or configured to be readily installed and removed from the cartridge channel jaw. Upon installation of the staple cartridge assembly 22050 into the cartridge channel jaw 22020, the surgical stapling assembly 22000 can be used to clamp, cut, and staple patient tissue. Details of various surgical stapling assemblies, components, and systems can be seen in U.S. Patent Application Publication No. 2021/0059672, which is hereby incorporated by reference in its entirety herein.

The cartridge channel jaw 22020 comprises a bottom 22031 and channel sidewalls 22034 extending from the bottom 22031. The bottom 22031 and the sidewalls 22034 define a cavity 22035 within which the staple cartridge assembly 22050 is configured to be positioned. The bottom 22031 comprises a cartridge-supporting surface 22032 and a longitudinal slot 22033 configured to receive at least a portion of a firing driver therein during a firing stroke. The firing driver may comprise a bar, a rod, a beam, an I-beam, and/or a tissue cutting knife, for example. The staple cartridge assembly 22050 comprises a cartridge body 22051 including a deck 22052 having staple cavities 22053 defined therein and a longitudinal slot 22054 defined in the deck 22052 configured to receive at least a portion of the firing driver during the firing stroke. The staple cartridge assembly 22050 further comprises a sled 22060 movable through the cartridge body 22051 by the firing driver during the firing stroke to engage staple drivers 22070 movably positioned in the staple cavities 22053 and drive staples 22001 stored in the staple cavities 22053 out of the cartridge body 22051.

Referring to FIG. 2, the sled 22060 comprises a bottom 22061 translatable longitudinally between the cartridge body 22051 and the cartridge channel 22030 and a plurality of ramped wedges, or sled ramps, 22062 extending upwardly from the bottom 22061. Further to the above, the ramped wedges 22062 are configured to sequentially lift the staple drivers 22070 from an unfired position (FIG. 2) to a fired position as the sled 22060 is moved through the cartridge body 22051 by the firing driver. As such, the staple drivers 22070 push the staples 22001 toward and against forming pockets defined in the anvil jaw 22022 to deform the staples 22001 into a formed configuration, such as a B-shaped configuration, for example.

Referring again to FIG. 2, each staple driver 22070 comprises a plurality of support columns 22071, each of which is configured to support a staple thereon. Each support column 22071 can comprise a trough or cradle defined in a top surface thereof that is configured to receive a base of a staple 22001 therein. Each staple driver 22070 further comprises web portions 22072 extending laterally between the support columns 22071. The web portions 22072 are configured to be contacted by the ramped wedges 22062 of the sled 22060 during the firing stroke to lift the staple drivers 22070 relative to the cartridge body 22051. The staple cartridge assembly 22050 comprises six longitudinal rows of staple cavities where each side of the staple cartridge assembly 22050 comprises three longitudinal rows of staple cavities. More specifically, the cartridge body 22051 has two sides—one on each side of the longitudinal slot 22054—where each side has an inner row of staple cavities adjacent the longitudinal slot 22054, an outer row of staple cavities, and an intermediate row of staple cavities positioned intermediate the inner row and the outer row. The staple cavities in the inner row and the staple cavities in the outer row are aligned laterally with one another. The staple cavities in the intermediate row are not laterally aligned with the staple cavities in the inner row and the outer row. Rather, the staple cavities in the intermediate row are shifted longitudinally, or longitudinally offset, with respect to the staple cavities in the inner row and the outer row. Because the intermediate row of staple cavities is longitudinally offset, an intermediate support column is not seen in the cross-sectional view of FIG. 2.

Referring again to FIG. 2, the cartridge body 22051 further comprises a plurality of longitudinally-extending cartridge walls 22055, 22056, 22057 extending downwardly from the deck 22052. Defined between the cartridge walls 22055, 22056, 22057 are longitudinal slots, or cavities, within which the ramped wedges 22062 of the sled 22060 are configured to translate during the staple firing stroke. Cartridge walls 22055 comprise inner cartridge walls that define the longitudinal slot 22054, cartridge walls 22056 comprise intermediate cartridge walls, and cartridge walls 22057 comprise outer cartridge walls adjacent the channel sidewalls 22034. The intermediate cartridge walls 22056 are positioned laterally between the inner cartridge walls 22055 and the outer cartridge walls 22057.

The inner cartridge walls 22055 comprise an inner lateral width W1. The intermediate cartridge walls 22056 comprise a intermediate lateral width W2. The outer cartridge walls 22057 comprise an outer lateral width W3. The inner lateral width W1 is wider than the intermediate lateral width W2 and the intermediate lateral width W2 is wider than the outer lateral width W3. Such a variance in lateral widths between the cartridge walls 22055, 22056, 22057 defines a varying lateral width gradient so as to provide thicker cartridge walls closer to the longitudinal slot 22054 than the channel sidewalls 22034. Providing thicker cartridge walls closer to the longitudinal slot 22054 can help reduce cartridge deflection, twisting, and/or collapsing within the staple cartridge assembly 22050.

As discussed above, referring again to FIG. 2, the inner cartridge walls 22055 extend downwardly from the deck 22052 of the cartridge body 22051. As can be seen in FIG. 2, a portion of the sled 22060 extends under the inner cartridge walls 22055. When the deck 22052 is subjected to a compressive load, for example, the inner cartridge walls 22055 can be in contact with the sled 22060. The inner cartridge walls 22055 and the sled 22060 can be sized and configured such that the sled 22060 is not in contact with the inner cartridge walls 22055 until the cartridge body 22051 deflects under load. The inner cartridge walls 22055 can be in contact with the sled 22060 prior the cartridge body 22051 deflecting under load. Similarly, the intermediate cartridge walls 22056 can be in contact with the sled 22060 when the deck 22052 is subjected to a compressive load. The intermediate cartridge walls 22056 and the sled 22060 can be sized and configured such that the sled 22060 is not in contact with the intermediate cartridge walls 22056 until the cartridge body 22051 deflects under load. The intermediate cartridge walls 22056 can be in contact with the sled 22060 prior the cartridge body 22051 deflecting under load.

When the cartridge body 22051 deflects under load and the inner cartridge walls 22055 and the intermediate cartridge walls 22056 push downwardly on the sled 22060, as described above, the sled 22060 is in contact with and supported by the cartridge support surface 22032 of the channel jaw 22030. The inner cartridge walls 22055 and the intermediate cartridge walls 22056 can comprise pillars that stiffen the staple cartridge assembly 22050. Referring to the cross-section of the staple cartridge assembly 22050 depicted in FIG. 2, the inner cartridge walls 22055 have a pillar length L1 as measured downwardly from the bottom of the deck 22032. Similarly, the intermediate cartridge walls 22056 have a pillar length L2 as measured downwardly from the bottom of the deck 22032. The pillar length L1 of the inner cartridge walls 22055 is constant along the longitudinal length of the cartridge body 22050, i.e., between the proximal and distal ends of the cartridge body 22050; however, the pillar length L1 of the inner cartridge walls 22055 may be different along the longitudinal length of the cartridge body 22050. Similarly, the pillar length L2 of the intermediate cartridge walls 22056 is constant along the longitudinal length of the cartridge body 22050; however, the pillar length L2 of the intermediate cartridge walls 22056 may be different along the longitudinal length of the cartridge body 22050.

Moreover, further to the above, when a compressive load is applied to the deck 22052, the outer cartridge walls 22057 are in contact with and are supported by the cartridge support surface 22032 of the channel jaw 22030. The outer cartridge walls 22057 can comprise pillars that support the deck 22052. In the cross-section depicted in FIG. 2, the outer cartridge walls 22057 are defined by a pillar length L3. Similar to the above, the pillar length L3 is constant along the longitudinal length of the cartridge body 22050; however, the pillar length L3 of the outer cartridge walls 22057 may be different along the longitudinal length of the cartridge body 22050. A staple cartridge can comprise a pan attached to and extending under the cartridge body, the sled 22060 is pushed downwardly against the pan and the outer cartridge walls 22057 are supported by the pan which are, in turn, supported by the cartridge support surface 22032.

Further to the above, the inner cartridge walls 22055, the intermediate cartridge walls 22056, the outer cartridge walls 22057, and the sled 22060 co-operate to support the cartridge body 22051. The inner cartridge walls 22055, the intermediate cartridge walls 22056, the outer cartridge walls 22057, and the sled 22060 can co-operate to support the cartridge body 22051 within a support plane that is transverse to the longitudinal axis of the staple cartridge assembly 22050. The cross-section of the staple cartridge assembly 22050 in FIG. 2 is taken along such a plane. Referring to FIG. 2, a longitudinal axis LA of the staple cartridge assembly 22050 is defined by the longitudinal slot 22054 which extends along the center of the cartridge body 22051 and the support plane of FIG. 2 is orthogonal to the longitudinal axis LA. In this support plane, the inner cartridge walls 22055 have a lateral width W1, the intermediate cartridge walls 22056 have a lateral width W2, and the outer cartridge walls 22057 have a lateral width W3. Notably, the lateral width W1 is constant along the entire pillar length L1 of the inner cartridge walls 22055 in this support plane. However, the lateral width W1 of an inner cartridge wall 22055 may not be constant along its entire pillar length L1. Similarly, the lateral width W2 is constant along the entire pillar length L2 of the intermediate cartridge walls 22056 and the lateral width W3 is constant along the entire pillar length L3 of the outer cartridge walls 22057 in this support plane. Whether or not the lateral width W1 of an inner cartridge wall 22055 is constant along the pillar length L1, an average lateral width of the inner cartridge wall 22055, i.e., the pillar width PW1, can be calculated along the pillar length L1. Similarly, an average lateral width of an intermediate cartridge wall 22056, i.e., the pillar width PW2, can be calculated along the pillar length L2 and an average lateral width of an outer cartridge wall 22057, i.e., the average pillar width PW3, can be calculated along the pillar length L3. Further to the above, the average pillar width PW1 of the inner cartridge walls 22055 may be wider than the average pillar width PW2 of the intermediate cartridge walls 22056, and the average pillar width PW2 of the intermediate cartridge walls 22056 is wider than the outer cartridge walls 22057.

Further to the above, the support plane depicted in FIG. 2 extends through, or transects, the inner cartridge walls 22055, the intermediate cartridge walls 22056, the outer cartridge walls 22057, and the sled 22060. During a staple firing stroke, the sled 22060 moves from a proximal unfired position at the proximal end of the cartridge body 22051 to a distal fired position at the distal end of the cartridge body 22051. As a result, the region in which the sled 22060 supports the cartridge body 22051 moves from the proximal end of the cartridge body 22051 to the distal end of the cartridge body 22051 during the staple firing stroke. Moreover, as a result, a support plane orthogonal to the longitudinal axis LA can move from the proximal end of the cartridge body 22051 to the distal end of the cartridge body 22051. As such, the support plane can move with the sled 22060 during the staple firing stroke from the proximal unfired position of the sled 22060 to the distal fired position of the sled 22060.

Further to the above, the lateral width W1 and/or the pillar width PW1 of the inner cartridge walls 22055 is constant along the longitudinal length thereof. As a result, the lateral width W1 and/or the pillar width PW1 of the inner cartridge walls 22055 is the same at the proximal end of the staple firing stroke as the distal end of the staple firing stroke. The lateral width W1 and/or the pillar width PW1 of the inner cartridge walls 22055 may not be constant along the longitudinal length thereof. The pillar width PW1 of the inner cartridge walls 22055 at the proximal end of the staple firing stroke may be wider than the pillar width PW1 of the inner cartridge walls 22055 at the distal end of the staple firing stroke. Similarly, the lateral widths W2 and W3 and/or the pillar widths PW2 and PW3 of the cartridge walls 22056 and 22057, respectively, are constant along the longitudinal length thereof. As a result, the lateral widths W2 and W3 and/or the pillar widths PW2 and PW3 of the cartridge walls 22056 and 22057 are the same at the proximal end of the staple firing stroke as the distal end of the staple firing stroke. The lateral widths W2 and W3 and/or the pillar widths PW2 and PW3 of the cartridge walls 22056 and 22057 may not be constant along the longitudinal length thereof. As such, the pillar width PW2 of the intermediate cartridge walls 22056 at the proximal end of the staple firing stroke may be wider than the pillar width PW2 of the intermediate cartridge walls 22056 at the distal end of the staple firing stroke. Likewise, the pillar width PW3 of the outer cartridge walls 22057 at the proximal end of the staple firing stroke may be wider than the pillar width PW3 of the outer cartridge walls 22057 at the distal end of the staple firing stroke.

Further to the above, referring again to FIG. 2, the cartridge body 22051 comprises two inner cartridge walls 22055 that have the same lateral width W1 and pillar width PW1 for any given support plane that is orthogonal to the longitudinal axis LA. Such an arrangement can permit the cartridge body 22051 to deflect symmetrically when subjected to a compressive load. However, one of the inner cartridge walls 22055 can have a different lateral width W1 and/or pillar width PW1 than the other inner cartridge wall 22055. Similarly, the cartridge body 22051 comprises two intermediate cartridge walls 22056 that have the same lateral width W2 and pillar width PW2 and two outer cartridge walls 22057 that have the same lateral width W3 and pillar width PW3 for any given support plane that is orthogonal to the longitudinal axis LA. One of the intermediate cartridge walls 22056 can have a different lateral width W2 and/or pillar width PW2 than the other intermediate cartridge wall 22056 and/or one of the outer cartridge walls 22057 can have a different lateral width W3 and/or pillar width PW3 than the other outer cartridge wall 22057.

Further to the above, the cartridge channel jaw 22020 defines a lateral support datum LSD along which a configuration of components of the cartridge channel jaw 22020 can aid in countering lateral cartridge deflection, twisting, and/or collapsing, for example, of the staple cartridge assembly 22050. Material, via the components of the staple cartridge assembly 22050, is presented in the lateral support datum LSD to consume laterally-presented spaces, or cavities, along the lateral support datum LSD thereby providing a path for laterally-induced force or stress to be transferred to the channel sidewalls 22034 of the channel jaw 22030. For instance, the cartridge body 22051 comprises staple cavities 22053 defined therein and staple drivers 22070, which move within the staple cavities 22053, that are sized and configured such that support columns 22071 of the staple drivers 22070 consume the empty spaces created by the staple cavities 22053. As such, as a result, the staple drivers 22070 comprise surfaces that are in abutting contact with the inner cartridge walls 22055, the intermediate cartridge walls 22056, and the outer cartridge walls 22057 such that the staple drivers 22070 provide lateral support to the cartridge body 22051. Moreover, the staple drivers 22070 comprise web portions 22052 that are slidingly engaged with the intermediate cartridge walls 22056 which provide lateral support to the cartridge body 22051. Also, the central portion 22063 of the sled 22060 is fitted in the longitudinal slot 22054 within the lateral support datum LSD so as to provide lateral support to the cartridge body 22051 within the longitudinal slot 22054.

Under a clamping load at the location within which the cross-sectional view of FIG. 2 is taken, for example, the cartridge walls may deflect inwardly into the longitudinal slot 22054 and/or outwardly toward the channel sidewalls 22034. Without material in each laterally-presented space between the longitudinal slot 22054 and the channel sidewalls 22034, the cartridge body 22051 may collapse inwardly on itself an/or outwardly toward the channel sidewalls 22034. With material in each laterally-presented space along the lateral support datum LSD by, for example, the central portion 22063 of the sled 22060, the inner cartridge walls 22055, the support columns 22071, the web portions 22072 of the staple drivers 22070, the intermediate cartridge walls 22056, and the outer cartridge walls 22057, the load is transferred through these components and to the channel sidewalls 22034. The channel sidewalls 22034 can be comprised of a stronger, or stiffer, material relative to the staple cartridge assembly and can absorb and/or effectively counter the clamping load.

The absorption of the clamping load by the channel sidewalls 22034 can occur throughout the firing stroke by utilizing one or more lateral support datum LSD. The lateral support datum LSD can be dynamically sustained with the central portion 22063 of the sled 22060 and with the staple drivers 22070 being lifted or driven by the sled 22060 such that the lateral support datum LSD not only moves longitudinally through the staple cartridge assembly 22050 during the firing stroke but also moves vertically as the staple drivers 22070 are lifted relative to the cartridge body 22051 and the staples 22001 are fired.

Figure 3:
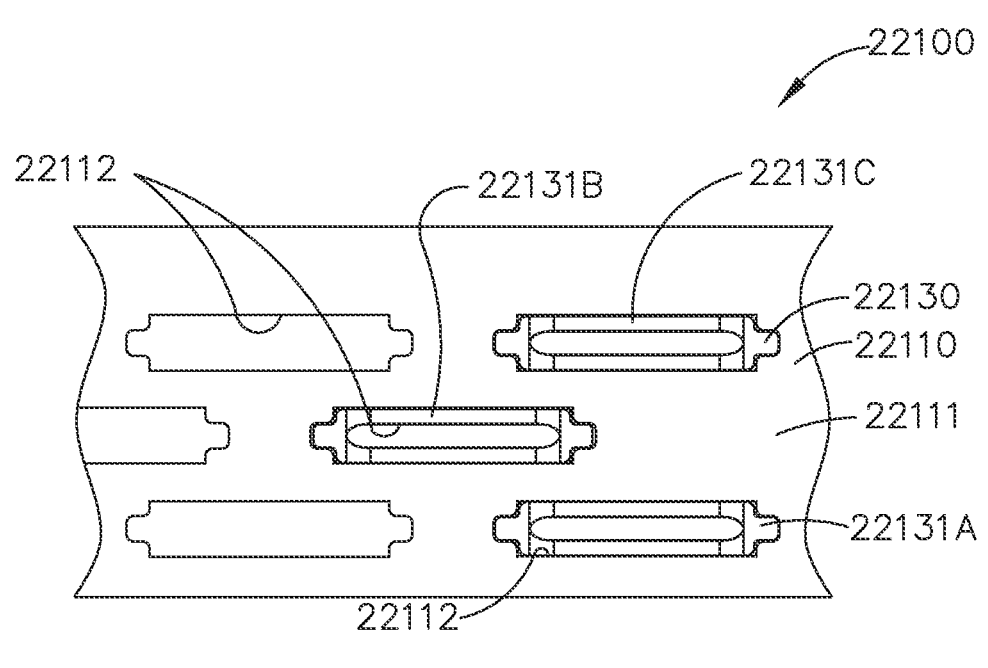
FIG. 3 is a partial top view of a cartridge body and a staple driver of a staple cartridge in accordance with the present disclosure.
Figure 4:
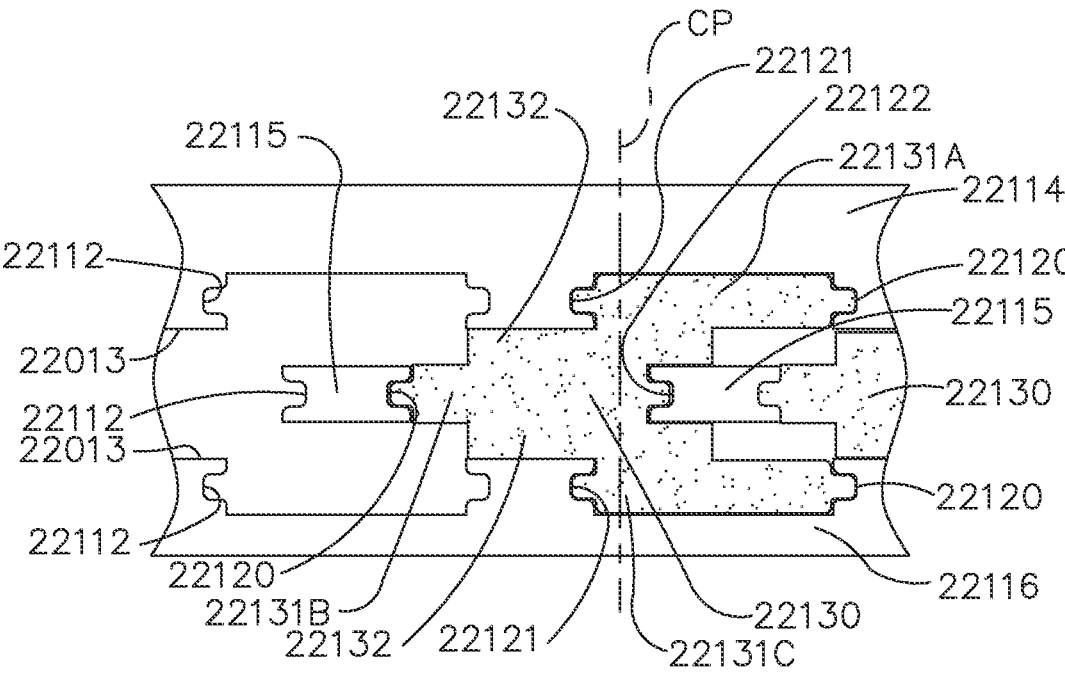
FIG. 4 is a partial bottom view of the staple cartridge of FIG. 3.

FIGS. 3 and 4 depict a staple cartridge assembly 22100 comprising a cartridge body 22110 and a plurality of staple drivers 22130 configured to be sequentially lifted relative to the cartridge body 22110 by a sled during a staple firing stroke. The cartridge body 22110 comprises a deck 22111 configured to support patient tissue and a plurality of staple cavities 22112 defined in the deck 22111. The cartridge body 22110 further comprises inner cartridge walls 22114, intermediate cartridge wall pillars 22115, and outer cartridge walls 22116. Each staple driver 22130 is configured to support and drive three staples; however, one or more staple drivers of the staple cartridge assembly 22100 are configured to support and drive more than three staples or less than three staples. Each staple driver 22130 comprises an inner support column 22131A, an intermediate support column 22131B, and an outer support column 22131C. The inner support column 22131A and the outer support column 22131C are proximal to the intermediate support column 22131B. The support columns 22131A, 22131B, 22131C are connected by driver bridges 22132. The driver bridges 22132 can be configured to be engaged by corresponding ramps defined on the sled during the staple firing stroke to lift the staple driver 22130, and the staples supported thereon, relative to the cartridge body 22110.

As a staple driver 22130 is contacted by a sled ramp, the staple driver 22130 may roll distally or, in other words, the proximal end of the staple driver 22130 may lift upwardly above the distal end. The staple cartridge assembly 22100 comprises a plurality of surfaces 22120 and a plurality of interaction surfaces 22121, 22122 between the staple driver 22130 and the cartridge body 22110. The surfaces 22120 are sized and configured so as to reduce and/or eliminate contact between the cartridge body 22110 and the staple driver 22130 at the surfaces 22120. The interaction surfaces 22121, however, are where the staple driver 22130 is configured to roll against, and be supported by, the cartridge body 22110 while the staple driver 22130 is being lifted upwardly during the staple firing stroke. The interaction surfaces 22122 are also configured to engage the cartridge body 22110 and provide a roll-countering force to counter the reaction force produced at the interaction surfaces 22121. Notably, the interaction surfaces 22121 and 22122 between the staple driver 22130 and the cartridge body 22110 are adjacent to a center plane CP of the staple driver 22130 whereas the surfaces 22120 are positioned further away from the center plane CP than the interaction surfaces 22120. Such an arrangement can reduce the roll of the staple drivers 22130 as the staple drivers 22130 are being lifted during the staple firing stroke.

As described above, a cartridge body of a staple cartridge assembly can comprise a unitary plastic body. As described above, such a cartridge body can be manufactured using an injection molding process, for example. A cartridge body can be manufactured using an insert molding process where a reinforcing material is at least partially encapsulated in a cartridge body. The inner cartridge walls 22114, the intermediate cartridge wall pillars 22115, and the outer cartridge walls 22116 can comprise material reinforcement molded into the structures themselves. Such reinforcement material can reduce deflection, collapsing, and/or twisting within the cartridge body. The reinforcement material can be oriented in a direction that is aligned with a high force vector and/or a direction that experiences a high degree of strain. A reinforcement material can be positioned along the sides of the longitudinal slot defined in the cartridge body that is configured to receive a firing driver.

Figure 5:
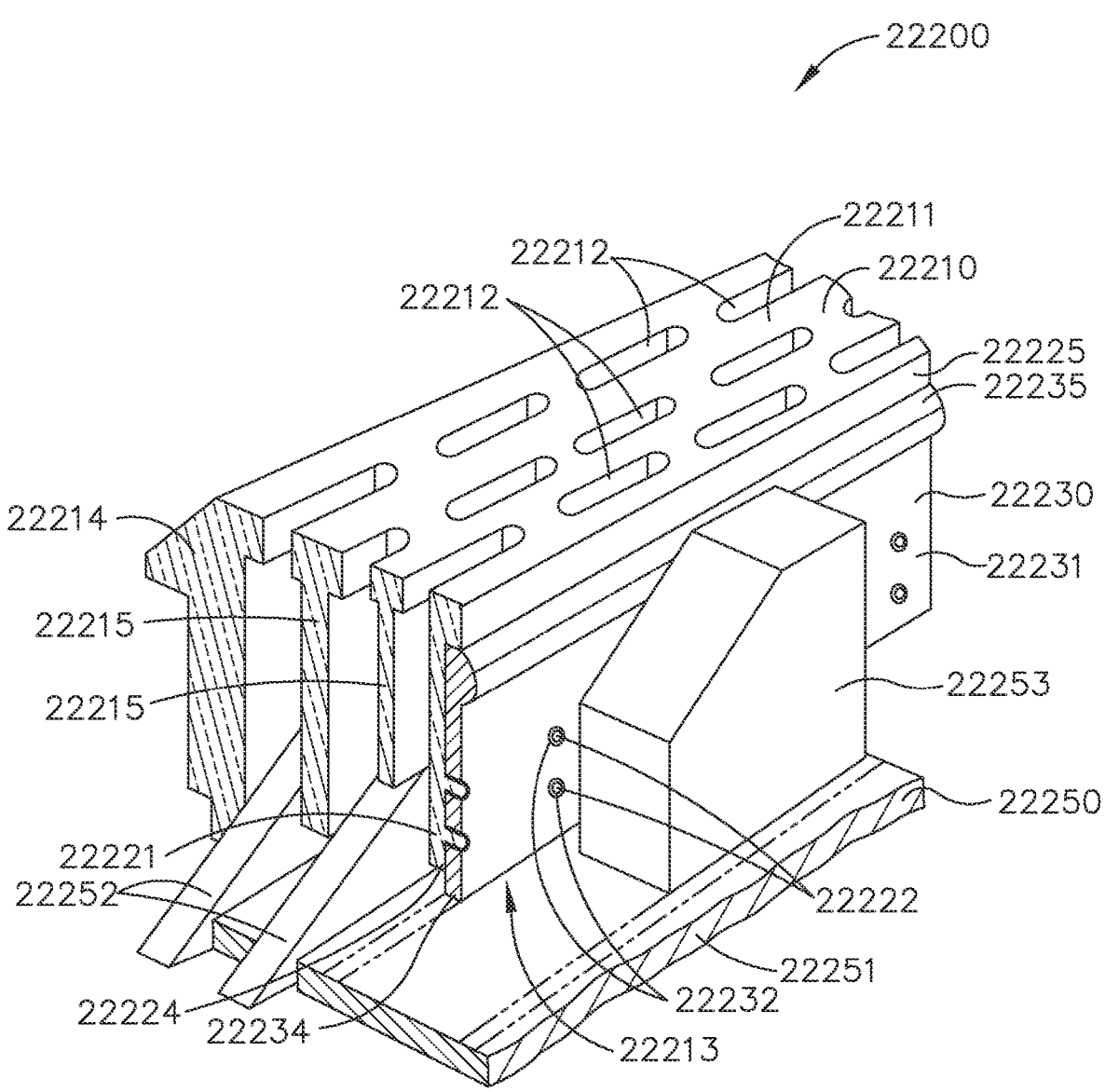
FIG. 5 is a partial cross-sectional perspective view of a staple cartridge comprising a cartridge body, a sled, and a support insert positioned within a longitudinal slot of the cartridge body in accordance with the present disclosure.
Figure 6:
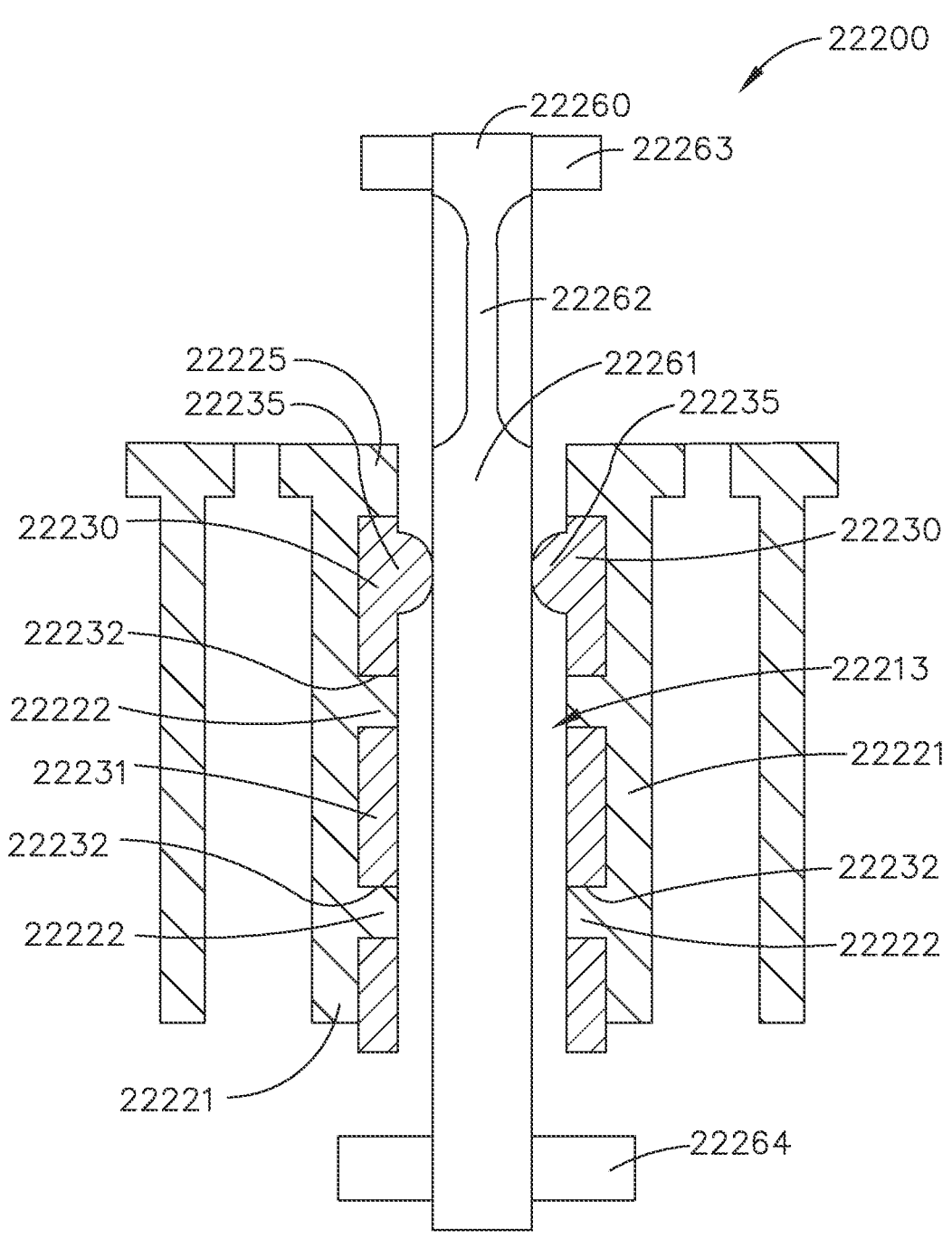
FIG. 6 is a cross-sectional view of a surgical stapling assembly comprising the staple cartridge assembly of FIG. 5 and a distal I-beam head of a firing driver.

FIGS. 5 and 6 depict a surgical stapling assembly 22000 comprising a staple cartridge 22210 and a firing driver 22260 movable distally to fire the staple cartridge 22210, cammingly hold opposing jaws in a fully clamped position, and cut patient tissue captured between the jaws during a staple firing stroke, as described in greater detail further below. The staple cartridge 22210 comprises a cartridge body 22211 including staple cavities 22212 defined therein, a plurality of staples removably stored in the staple cavities 22212, and staple drivers movable to eject the staples from the staple cavities 22212 during the staple firing stroke. The staple cartridge assembly 22210 further comprises a sled 22250 movable through the cartridge body 22211 by the firing driver 22260 during the staple firing stroke to sequentially lift the staple drivers and staples toward an anvil jaw positioned opposite the staple cartridge 22200. Alternatively, the staples of a staple cartridge can be configured to be directly driven by a sled. As such, the staple cartridge does not have staple drivers.

The cartridge body 22211 further comprises a longitudinal slot 22213 configured to receive the firing driver 22260 and at least a portion of the sled 22250 during the staple firing stroke. The cartridge body 22211 also comprises a plurality of longitudinally-extending cartridge walls including outer cartridge walls 22214, intermediate cartridge walls 22215, and inner cartridge walls 22221. When the staple cartridge 22200 is installed in a cartridge channel jaw of a surgical stapling instrument, the outer cartridge walls 22214 are supported by walls of the cartridge channel jaw. The intermediate cartridge walls 22215 are positioned between the outer cartridge walls 22214 and the inner cartridge walls 22221. The inner cartridge walls 22221 are positioned adjacent the longitudinal slot 22213. The cartridge walls

22214, 22215, 22221 define longitudinally-extending cavities therebetween that are configured to receive sled ramps 22252 of the sled 22250 during the staple firing stroke.

The sled 22250 comprises a bottom portion 22251 and a central portion 22253 extending from the bottom portion 22251. The central portion 22253 is configured to traverse the longitudinal slot 22213 during the staple firing stroke. The sled ramps 22252 also extend from the bottom portion 22251 and are configured to lift the staple drivers as the sled 22250 is translated through the cartridge body 22211 during the staple firing stroke. It should be appreciated that the view presented in FIG. 5 is a partial cross-sectional view of the surgical stapling assembly 22200 and that the surgical stapling assembly 22200 is laterally-symmetric relative to a longitudinal axis defined by the longitudinal slot 22213 such that the staple cartridge 22210 comprises longitudinal rows of cavities and cartridge walls on the opposite sides of the longitudinal slot 22213. Likewise, the sled 22250 comprises sled ramps 22252 on opposing sides thereof that are configured to eject staples on the opposite side of the longitudinal slot 22213.

Further to the above, the firing driver 22260 comprises a distal I-beam head comprising a body portion 22261, a cutting edge 22262 defined on a distal end of the body portion 22261 to cut patient tissue captured between opposing jaws, and jaw cams 22263, 22264 configured to cammingly hold the opposing jaws in a fully-clamped configuration during the staple firing stroke. Also further to the above, the staple cartridge 22210 can be subject to clamping loads which may encourage the cartridge body 22211 to deflect. To prevent or reduce such deflection, the staple cartridge 22210 further comprises a support insert 22230 that at least partially defines the longitudinal slot 22213. The support insert 22230 can counter inward deflection of the inner cartridge wall 22221. The support insert 22230 may be comprised of metal, for example. The support insert 22230 may be molded within the inner cartridge wall 22221. The support insert 22230 may be snap-fit with and/or press-fit to the cartridge body 22211 to and/or attached to the cartridge body 22211 using at least one adhesive, for example.

The support insert 22230 comprises a secondary wall structure adjacent the inner cartridge wall 22221. The support insert 22230 comprises a primary wall portion 22231 and an upper support rail 22235. The primary wall portion 22231 is adjacent the inner cartridge wall 22221 and the upper support rail 22235 is adjacent an upper ledge 22225 of the inner cartridge wall 22221. The support insert 22230 further comprises apertures 22232 defined therein configured to receive corresponding posts 22222 extending inwardly toward the longitudinal slot 22213 from the inner cartridge wall 22221. The posts 22222 and apertures 22232 are configured to align and/or hold the support insert 22230 to the inner cartridge wall 22221. The upper support rail 22235 extends laterally inwardly into the longitudinal slot 22213 such that the sled 22250 and/or firing driver 22260 are guided by the support rail 22235 during the staple firing stroke and, concurrently, the sled 22250 and/or firing driver 22260 provide support to the cartridge body 22211.

Further to the above, the staple cartridge 22210 comprises two support inserts 22230—one on each side of the longitudinal slot 22213—with each having an inwardly-facing support rail 22235. The support rails 22235 extend along the entire length of the support inserts 22230 and are supported by the sled 22250 and/or firing driver 22260 throughout the entire length of the staple firing stroke. The support rails 22235 may not extend along the entire length of the support inserts 22230. The opposing support rails 22235 can comprise longitudinal gaps defined therein such that the sled 22250 and/or firing driver 22260 are not in contact with the support rails 22235 during low-load portions of the staple firing stroke but are in contact with the support rails 22235 during high-load portions of the staple firing stroke. The sled 22250 and firing driver 22260 may not be engaged with the support rails 22235 during the initial 15 mm of the staple firing stroke but are engaged with the support rails 22235 distal to the initial 15 mm of the staple firing stroke, for example.

The primary wall portion 22231 further comprises a bottom 22234 extending below a bottom 22224 of the inner cartridge wall 22221 that can transfer loads to the cartridge channel jaw outside of the cartridge body 22211. Clamping loads can be transferred through the inner cartridge wall 22221, for example, through the posts 22222 and down to the bottom portion 22251 of the sled 22250. A cartridge pan and/or a cartridge channel can be positioned directly beneath the bottom portion 22251 of the sled 22250 such that the bottom portion 22251 slides against and is supported by the cartridge pan and/or cartridge channel. As such, the clamping load can be transferred through the support insert 22230, through the bottom portion 22251 of the sled 22250, and into the cartridge channel and/or cartridge pan, for example.

The surgical stapling assembly 22200 can provide cartridge deflection support without introducing excessive frictional forces to the firing stroke. Controlling the contact points where clamping load can be countered can help reduce component wear and firing malfunctions, for example. As discussed herein, cartridge deflection, collapsing, and/or twisting can cause staples to be ejected out of alignment with corresponding forming pockets defined in the anvil jaw and thus cause malformed staples and possibly inadequately stapled tissue, for example. Support inserts can be provided in specific portions of the firing stroke. A support insert may be positioned only in the proximal portion of the firing stroke and not the distal portion of the firing stroke.

Figure 7:
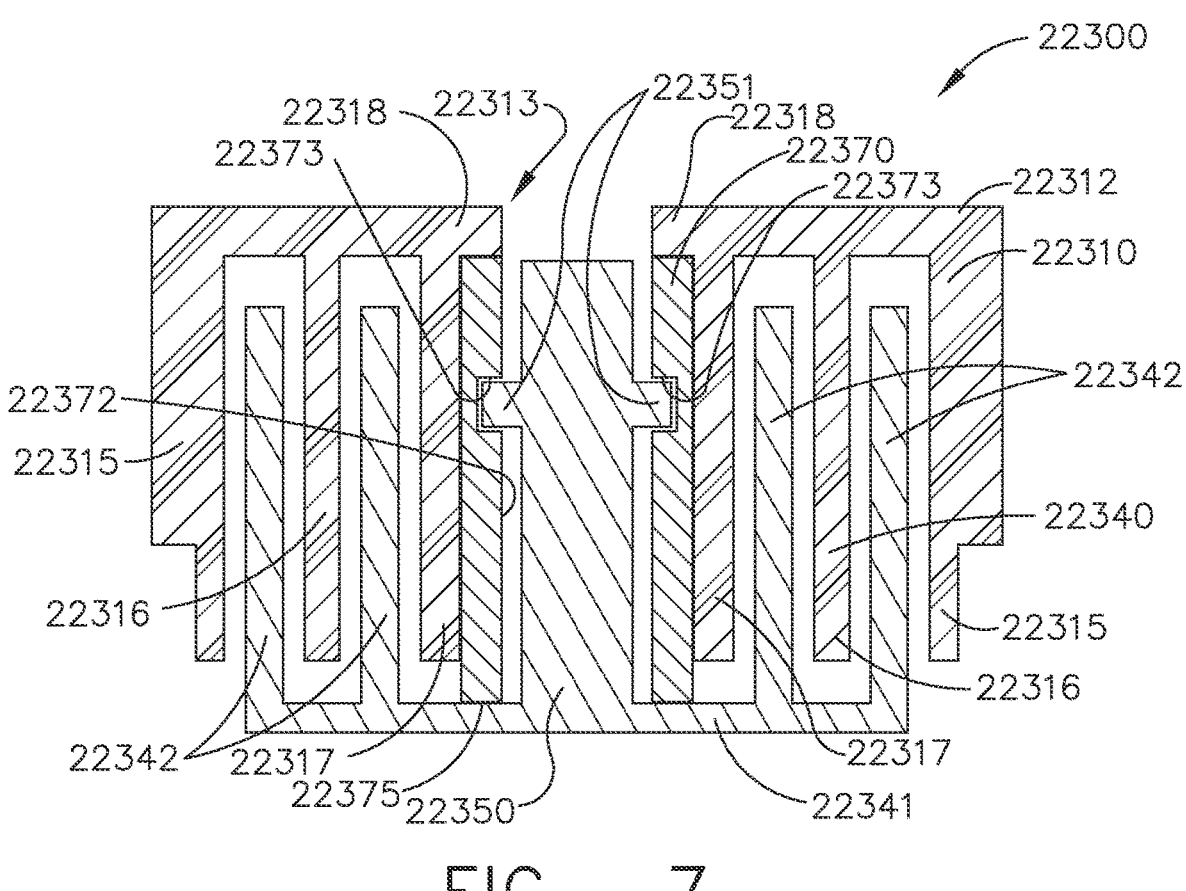
FIG. 7 is a cross-sectional view of a staple cartridge comprising a cartridge body, a sled movable through the cartridge body, and support inserts positioned within a longitudinal slot of the cartridge body in accordance with the present disclosure.
Figure 8:
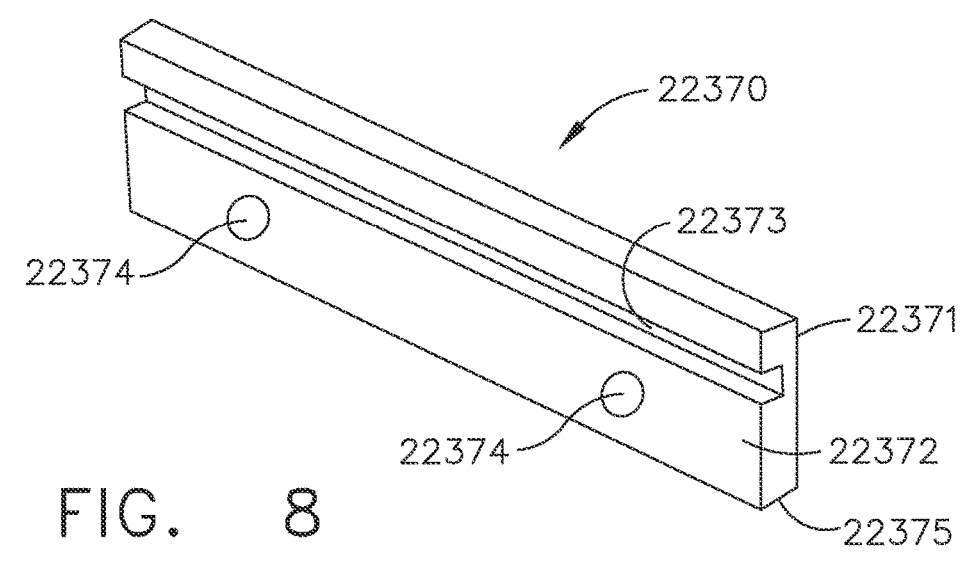
FIG. 8 is a perspective view of one of the support inserts of FIG. 7.

FIGS. 7 and 8 depict a staple cartridge 22300 for use with a surgical stapling instrument. The staple cartridge 22300 comprises a cartridge body 22310, a sled 22340 movable through the cartridge body 22310 to eject staples from the cartridge body 22310, and support inserts 22370 positioned within the cartridge body 22310. The cartridge body 22310 comprises a tissue-supporting deck 22312 against which tissue can be clamped and a longitudinal slot 22313 extending through the cartridge body 22310. The longitudinal slot 22313 is configured to receive at least a portion of the sled 22340 and a firing driver such as, for example, a distal I-beam head. The cartridge body 22310 further comprises a plurality of longitudinally-extending cartridge walls comprising outer cartridge walls 22315, intermediate cartridge walls 22316, and inner cartridge walls 22316. The sled 22340 comprises a bottom portion 22341 and ramps 22342 extending upwardly from the bottom portion 22341 into longitudinal cavities defined between the cartridge walls 22315, 22316, 22317 that sequentially lift and eject staples from the cartridge body 22310.

When the staple cartridge 22300 is seated in the cartridge channel of a surgical stapling instrument, the outer cartridge wall 22315 is supported by the walls of the cartridge channel. The sled 22340 further comprises a central rib 22350 positioned within the longitudinal slot 22313 such that the central rib 22350 translates within the longitudinal slot 22313 during a firing stroke. The sled 22340 is movable distally by a longitudinally-translatable firing driver such as a distal I-beam head, for example. The sled 22340 may be actuatable by a drive screw. In either event, the longitudinal slot 22313 is at least partially defined by support inserts 22370. The support inserts 22370 are positioned against the inner cartridge walls 22317 and ledges 22318 of the inner cartridge walls 22317. The support inserts 22370 may comprise a metal material, such as stainless steel, for example. The support inserts 22370 may be over molded onto the inner cartridge walls 22317.

Each support insert 22370 comprises an outer face 22371, an inner face 22372, and a longitudinally-extending channel 22373 defined in the inner face 22372. Each support insert 22370 further comprises a bottom support surface 22375 and fasteners 22374 configured to hold the support insert 22370 to the inner cartridge wall 22317. The fasteners 22374 may comprise any suitable type of fastener such as, for example, adhesive, screws, and/or rivets. The fasteners 22374 can comprise portions of the inner cartridge wall 22317 which are thermoplastically staked against the support insert 22370.

The support inserts 22370 are configured to transfer clamping loads from the cartridge body 22310 to the bottom portion 22341 of the sled 22340 and to an opposing support surface such as a staple cartridge-supporting surface of a cartridge channel, for example. The support inserts 22370 extend below the inner cartridge walls 22317 where the bottom support surfaces 22375 of the support inserts 22370 contact the top of the bottom portion 22341 of the sled 22340. The bottom surfaces of the cartridge walls 22315, 22316, 22317 can be sized and configured such that they cannot push downwardly on the sled 22340 when the staple cartridge 22300 is subject to load. As such, a large portion of the downward clamping force applied to the staple cartridge 22300 flows downwardly to the cartridge channel in and/or near the central or inner portion of the staple cartridge 22300.

The central rib 22350 of the sled 22340 further comprises lateral projections 22351. The lateral projections 22351 translate within the channels 22373 of the support inserts 22370 during the staple firing stroke. The lateral projections 22351 of the sled 22340 can engage the sidewalls of the channels 22373 which can align the sled 22340 relative to the cartridge body 22310 during the firing stroke. Engagement between the lateral projections 22351 and the sidewalls of the channels 22373 can reduce lateral and vertical deflection of the cartridge body 22310 during the staple firing stroke. As the sled 22340 is pushed distally through the staple firing stroke, the bottom support surfaces 22375 of the support inserts 22370 are slidably supported on the bottom portion 22341 of the sled 22340. Clamping loads experienced by the cartridge body 22310 can be transferred through the bottom portion 22341 by the bottom support surfaces 22375 of the support inserts 22370. In addition to or in lieu of the above, the firing driver pushing the sled 22340 distally can have lateral projections 22351 that translate within channels 22373 and engage the sidewalls of the channels 22373, as described above. When both the sled 22340 and the firing driver both have such lateral projections, the lateral projections on the firing driver can help further distribute clamping loads along a height of an end effector and act as a central camming member in between an upper jaw-camming member and a lower jaw-camming member of the firing driver.

Various aspects of the subject matter described herein are set out in the following examples.

Example 1—A surgical stapling assembly (22000, 22100, 22200, 22300), comprising a cartridge body (22051, 22110, 22210, 22310) comprising a deck (22052, 22211, 22312)

configured to support patient tissue, wherein the deck comprises a proximal end and a distal end, a plurality of staple cavities (22053, 22212) defined in the deck, a longitudinal slot (22054, 22213, 22313) defined in the deck, wherein the longitudinal slot extends from the proximal end toward the distal end, wherein the longitudinal slot defines a longitudinal axis, wherein the longitudinal slot is defined by an inner cartridge wall (22055), wherein the staple cavities are arranged in longitudinal rows on opposite sides of the longitudinal slot, and wherein the longitudinal slot is configured to receive at least a portion of a firing driver (22260) during a firing stroke, and an outer cartridge wall (22034) extending longitudinally between the proximal end and the distal end. The surgical stapling assembly further comprises a plurality of staples (22001) removably stored in the staple cavities, a plurality of staple drivers (22070), a sled (22060) movable longitudinally through the cartridge body from a proximal unfired position to a distal fired position by the firing driver to lift the staple drivers within the staple cavities to eject the staples from the staple cavities during the firing stroke, and a support plane that extends perpendicular to the longitudinal axis, wherein the sled is positioned under the inner cartridge wall in the support plane, wherein the inner cartridge wall comprises a first lateral pillar width and a first pillar height in the support plane, wherein the first lateral pillar width comprises an average lateral width of the inner cartridge wall along the first pillar height, wherein the outer cartridge wall comprises a second lateral pillar width and a second pillar height in the support plane, wherein the second lateral pillar width comprises an average lateral width of the outer cartridge wall along the second pillar height, and wherein the first lateral pillar width is wider than the second lateral pillar width.

Example 2—The surgical stapling assembly of Example 1, wherein the sled is engaged with the inner cartridge wall in the support plane.

Example 3—The surgical stapling assembly of Examples 1 or 2, wherein the support plane is at the proximal unfired position of the sled.

Example 4—The surgical stapling assembly of Examples 1, 2, or 3, wherein the support plane moves distally with the sled during the firing stroke.

Example 5—The surgical stapling assembly of Examples 1, 2, 3, or 4, wherein the cartridge body further comprises an intermediate cartridge wall (22056) situated laterally between the inner cartridge wall and the outer cartridge wall, and wherein the intermediate cartridge wall comprises a third lateral pillar width and a third pillar height in the support plane, wherein the third lateral pillar width comprises an average lateral width of the intermediate cartridge wall along the third pillar height, and wherein the third lateral pillar width is narrower than the first lateral pillar width and wider than the second lateral pillar width.

Example 6—The surgical stapling assembly of Examples 1, 2, 3, 4, or 5, further comprising a support insert (22230) positioned within the longitudinal slot.

Example 7—The surgical stapling assembly of Example 6, wherein the support insert comprises a material different than the cartridge body.

Example 8—The surgical stapling assembly of Examples 6 or 7, wherein the sled comprises a base (22251) comprising an upper surface that faces the deck, and wherein the upper surface of the base is configured to engage the bottom surface (22234) of the support insert during the firing stroke.

Example 9—The surgical stapling assembly of Examples 6, 7, or 8, wherein the cartridge body further comprises a ledge (22225) extending laterally into the longitudinal slot, wherein the support insert is positioned against the ledge.

Example 10—The surgical stapling assembly of Examples 6, 7, 8, or 9, wherein the support insert comprises a ridge (22235) extending longitudinally along a length of the support insert, wherein the ridge extends inwardly into the longitudinal slot, and wherein the sled comprises a base (22251), a plurality of ramped wedges (22252) extending from the base, and a central rib (22253) extending from the base that is configured to be received within the longitudinal slot, wherein the central rib is configured to engage the ridge of the support insert during the firing stroke.

Example 11—The surgical stapling assembly of Examples 6, 7, 8, 9, or 10, wherein an insert slot is defined in a longitudinal length of the support insert, and wherein the sled comprises a base (22341), a plurality of ramped wedges (22342) extending from the base, and a central rib (22350) extending from the base and configured to be received within the insert slot, wherein the central rib comprises a projection (22351) configured to engage the insert slot during the firing stroke.

Example 12—The surgical stapling assembly of Examples 1, 2, 3, 4, 5, 6, 7, 8, 9, 10, or 11 wherein each staple driver comprises a first driver column (22131A) configured to support a first staple of the plurality of staples within a first staple cavity of the plurality of staple cavities, wherein the first driver column comprises a first distal end and a first proximal end, a second driver column (22131C) configured to support a second staple of the plurality of staples within a second staple cavity of the plurality of staple cavities, wherein the second driver column comprises a second distal end and a second proximal end, and a third driver column (22131B) configured to support a third staple of the plurality of staples within a third staple cavity of the plurality of staple cavities, wherein the third driver column comprises a third distal end and a third proximal end, wherein the third driver column is positioned between the first driver column and the second driver column, wherein the second proximal end is distal to the first proximal end and the second proximal end, and wherein the first distal end and the third distal end are configured to engage the cartridge body as the staple driver is lifted from an unfired position to a fired position and a clearance is defined between the first proximal end and the cartridge body and the third proximal end and the cartridge body as the staple driver is lifted from the unfired position to the fired position.

Example 13—The surgical stapling assembly of Example 12, wherein the clearance comprises a first clearance, and wherein a second clearance is defined between the second distal end and the cartridge body as the staple driver is lifted from the unfired position to the fired position.

Example 14—The surgical stapling assembly of Examples 12 or 13, wherein the cartridge body is configured to counteract longitudinal rotation of the staple driver proximal end over distal end through engagement between the second proximal end and the cartridge body.

Example 15—The surgical stapling assembly of Examples 1, 2, 3, 4, 5, 6, 7, 8, 9, 10, 11, 12, 13, or 14, further comprising a pan attached to the cartridge body, wherein the cartridge body comprises a bottom opposite the deck, and wherein the pan is configured to prevent the staple drivers and the sled from falling out of the bottom of the cartridge body.

Example 16—A surgical stapling assembly comprising a cartridge body comprising a deck configured to support patient tissue, wherein the deck comprises a proximal end and a distal end, a plurality of staple cavities defined in the deck, a longitudinal slot defined in the deck, wherein the longitudinal slot extends from the proximal end toward the distal end, wherein the longitudinal slot defines a longitudinal axis, wherein the longitudinal slot is defined by an inner cartridge wall, wherein the staple cavities are arranged in longitudinal rows on opposite sides of the longitudinal slot, and wherein the longitudinal slot is configured to receive at least a portion of a firing driver during a firing stroke, and an outer cartridge wall extending longitudinally between the proximal end and the distal end. The surgical stapling assembly further comprises a plurality of staples removably stored in the staple cavities, a plurality of staple drivers, a sled movable longitudinally through the cartridge body from a proximal unfired position to a distal fired position by the firing driver to lift the staple drivers within the staple cavities to eject the staples from the staple cavities during the firing stroke, and a support plane that extends perpendicular to the longitudinal axis, wherein the sled is positioned under the inner cartridge wall in the support plane, wherein the inner cartridge wall comprises a first lateral pillar width and a first pillar height in the support plane, wherein the first lateral pillar width comprises an average lateral width of the inner cartridge wall along the first pillar height, wherein the outer cartridge wall comprises a second lateral pillar width and a second pillar height in the support plane, wherein the second lateral pillar width comprises an average lateral width of the outer cartridge wall along the second pillar height, and wherein the first lateral pillar width is wider than the second lateral pillar width.

Example 17—The surgical stapling assembly of Example 16, wherein the sled is engaged with the inner cartridge wall in the support plane.

Example 18—The surgical stapling assembly of Examples 16 or 17, wherein the support plane is at the proximal unfired position of the sled.

Example 19—The surgical stapling assembly of Examples 16, 17, or 18, wherein the support plane moves distally with the sled during the firing stroke.

Example 20—The surgical stapling assembly of Examples 16, 17, 18, or 19, wherein the cartridge body further comprises an intermediate cartridge wall (22056) situated laterally between the inner cartridge wall and the outer cartridge wall, and wherein the intermediate cartridge wall comprises a third lateral pillar width and a third pillar height in the support plane, wherein the third lateral pillar width comprises an average lateral width of the intermediate cartridge wall along the third pillar height, and wherein the third lateral pillar width is narrower than the first lateral pillar width and wider than the second lateral pillar width.

Example 21—The surgical stapling assembly of Examples 16, 17, 18, 19, or 20, further comprising a support insert positioned within the longitudinal slot.

Example 22—The surgical stapling assembly of Example 21, wherein the support insert comprises a material different than the cartridge body.

Example 23—The surgical stapling assembly of Examples 21 or 22, wherein the sled comprises a base comprising an upper surface that faces the deck, and wherein the upper surface of the base is configured to engage the bottom surface of the support insert during the firing stroke.

Example 24—The surgical stapling assembly of Examples 21, 22, or 23, wherein the cartridge body further comprises a ledge extending laterally into the longitudinal slot, wherein the support insert is positioned against the ledge.

Example 25—The surgical stapling assembly of Examples 21, 22, 23, or 24, wherein the support insert comprises a ridge extending longitudinally along a length of the support insert, wherein the ridge extends inwardly into the longitudinal slot, and wherein the sled comprises a base, a plurality of ramped wedges extending from the base, and a central rib extending from the base that is configured to be received within the longitudinal slot, wherein the central rib is configured to engage the ridge of the support insert during the firing stroke.

Example 26—The surgical stapling assembly of Examples 21, 22, 23, 24, or 25, wherein an insert slot is defined in a longitudinal length of the support insert, and wherein the sled comprises a base, a plurality of ramped wedges extending from the base, and a central rib extending from the base and configured to be received within the insert slot, wherein the central rib comprises a projection configured to engage the insert slot during the firing stroke.

Example 27—The surgical stapling assembly of Examples 16, 17, 18, 19, 20, 21, 22, 23, 24, 25, or 26, wherein each staple driver comprises a first driver column configured to support a first staple of the plurality of staples within a first staple cavity of the plurality of staple cavities, wherein the first driver column comprises a first distal end and a first proximal end, a second driver column configured to support a second staple of the plurality of staples within a second staple cavity of the plurality of staple cavities, wherein the second driver column comprises a second distal end and a second proximal end, and a third driver column configured to support a third staple of the plurality of staples within a third staple cavity of the plurality of staple cavities, wherein the third driver column comprises a third distal end and a third proximal end, wherein the third driver column is positioned between the first driver column and the second driver column, wherein the second proximal end is distal to the first proximal end and the second proximal end, and wherein the first distal end and the third distal end are configured to engage the cartridge body as the staple driver is lifted from an unfired position to a fired position and a clearance is defined between the first proximal end and the cartridge body and the third proximal end and the cartridge body as the staple driver is lifted from the unfired position to the fired position.

Example 28—The surgical stapling assembly of Example 27, wherein the clearance comprises a first clearance, and wherein a second clearance is defined between the second distal end and the cartridge body as the staple driver is lifted from the unfired position to the fired position.

Example 29—The surgical stapling assembly of Examples 27 or 28, wherein the cartridge body is configured to counteract longitudinal rotation of the staple driver proximal end over distal end through engagement between the second proximal end and the cartridge body.

Example 30—The surgical stapling assembly of Examples 16, 17, 18, 19, 20, 21, 22, 23, 24, 25, 26, 27, 28, or 29, further comprising a pan attached to the cartridge body, wherein the cartridge body comprises a bottom opposite the deck, and wherein the pan is configured to prevent the staple drivers and the sled from falling out of the bottom of the cartridge body.

Example 31—A surgical staple cartridge comprising a cartridge body comprising a deck configured to support patient tissue, wherein the deck comprises a proximal end and a distal end, a plurality of staple cavities defined in the deck, a longitudinal slot defined in the deck, wherein the longitudinal slot extends from the proximal end toward the distal end, wherein the longitudinal slot defines a longitudinal axis, wherein the longitudinal slot is defined by an inner wall, wherein the staple cavities are arranged in longitudinal rows on opposite sides of the longitudinal slot, and wherein the longitudinal slot is configured to receive at least a portion of a firing driver during a firing stroke. The cartridge body further comprises an outer wall extending longitudinally between the proximal end and the distal end. The surgical staple cartridge further comprises a plurality of staples removably stored in the staple cavities, a ramp movable longitudinally through the cartridge body from a proximal unfired position to a distal fired position by the firing driver to eject the staples from the staple cavities during the firing stroke, and a support plane that extends perpendicular to the longitudinal axis, wherein the sled is positioned under the inner wall in the support plane, wherein the inner wall comprises a first lateral pillar width and a first pillar height in the support plane, wherein the outer wall comprises a second lateral pillar width and a second pillar height in the support plane, and wherein the first lateral pillar width is wider than the second lateral pillar width.

Example 32—The surgical staple cartridge of Example 31, wherein the support plane moves distally with the sled during the firing stroke.

Example 33—A surgical staple cartridge comprising a cartridge body comprising a tissue-supporting surface configured to support patient tissue, wherein the tissue-supporting surface comprises a proximal end and a distal end, a plurality of staple cavities defined in the tissue-supporting surface, and a longitudinal slot defined in the tissue-supporting surface, wherein the longitudinal slot extends from the proximal end toward the distal end, wherein the longitudinal slot defines a longitudinal axis, wherein the longitudinal slot is defined by an inner lateral cartridge wall, wherein the staple cavities are arranged in longitudinal rows on opposite sides of the longitudinal slot, and wherein the longitudinal slot is configured to receive at least a portion of a firing driver during a firing stroke. The surgical staple cartridge further comprises a plurality of staples removably stored in the staple cavities, a sled movable longitudinally through the cartridge body from a proximal unfired position to a distal fired position by the firing driver to eject the staples from the staple cavities during the firing stroke, a support plane that extends perpendicular to the longitudinal axis, and a support insert positioned within the longitudinal slot, wherein the support insert comprises a material different than the cartridge body.

Example 34—The surgical staple cartridge of Example 33, wherein the support insert comprises a bottom configured to engage a cartridge channel of a stapling end effector within which the surgical staple cartridge is configured to be installed.

Example 35—The surgical staple cartridge of Example 34, wherein the sled is configured to engage the support insert during the firing stroke to resist deflection of the cartridge body.

Many of the surgical instrument systems described herein are motivated by an electric motor; however, the surgical instrument systems described herein can be motivated in any suitable manner. The surgical instrument systems described herein can be motivated by a manually-operated trigger, for example. The motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGE- MENTS, now U.S. Pat. No. 9,072,535, for example, discloses several examples of a robotic surgical instrument system in greater detail.

The surgical instrument systems described herein have been described in connection with the deployment and deformation of staples; however, the present disclosure may not be so limited. The present disclosure envisions that fasteners other than staples can be deployed, such as clamps or tacks, for example. Moreover, the present disclosure envisions utilizing any suitable means for sealing tissue. An end effector in accordance with the present disclosure can comprise electrodes configured to heat and seal the tissue. Also, an end effector in accordance with the present disclosure can apply vibrational energy to seal the tissue.

The entire disclosures of U.S. Pat. No. 11,589,865, entitled METHODS FOR CONTROLLING A POWERED SURGICAL STAPLER THAT HAS SEPARATE ROTARY CLOSURE AND FIRING SYSTEMS, which issued on Feb. 28, 2023, U.S. Pat. No. 6,978,921, entitled SURGICAL STAPLING INSTRUMENT INCORPORATING AN E-BEAM FIRING MECHANISM, which issued on Dec. 27, 2005, U.S. Pat. No. 10,213,203, entitled STAPLE CARTRIDGE ASSEMBLY WITHOUT A BOTTOM COVER, which issued on Feb. 26, 2019, U.S. Pat. No. 10,945,727, entitled STAPLE CARTRIDGE WITH DEFORMABLE DRIVER RETENTION FEATURES, which issued on Mar. 16, 2021, U.S. Pat. No. 11,234,698, entitled STAPLING SYSTEM COMPRISING A CLAMP LOCKOUT AND A FIRING LOCKOUT, which issued on Feb. 1, 2022, U.S. Pat. No. 11,540,826, entitled SURGICAL STAPLER END EFFECTOR SLED HAVING CARTRIDGE WALL SUPPORT FEATURE, which issued on Jan. 3, 2023, U.S. Pat. No. 10,299,792, entitled FASTENER CARTRIDGE COMPRISING NON-UNIFORM FASTENERS, which issued on May 28, 2019, U.S. Pat. No. 8,540,133, entitled STAPLE CARTRIDGE, which issued on Sep. 24, 2013, U.S. Pat. No. 9,788,835, entitled DEVICES AND METHODS FOR FACILITATING EJECTION OF SURGICAL FASTENERS FROM CARTRIDGES, which issued on Oct. 17, 2017, U.S. Pat. No. 10,105,142, entitled SURGICAL STAPLER WITH PLURALITY OF CUTTING ELEMENTS, which issued on Oct. 23, 2018, U.S. Pat. No. 10,537,324, entitled STEPPED STAPLE CARTRIDGE WITH ASYMMETRICAL STAPLES, which issued on Jan. 21, 2020, U.S. Pat. No. 7,669,746, entitled STAPLE CARTRIDGES FOR FORMING STAPLES HAVING DIFFERING FORMED STAPLE HEIGHTS, which issued on Mar. 2, 2010, U.S. Pat. No. 8,123,100, entitled SURGICAL STAPLING INSTRUMENTS INCLUDING A CARTRIDGE HAVING MULTIPLE STAPLE SIZES, which issued on Feb. 28, 2012, U.S. Pat. No. 7,407,075, entitled STAPLE CARTRIDGE HAVING MULTIPLE STAPLE SIZES FOR A SURGICAL STAPLING INSTRUMENT, which issued on Aug. 5, 2008, U.S. Pat. No. 10,085,749, entitled SURGICAL APPARATUS WITH CONDUCTOR STRAIN RELIEF, which issued on Oct. 2, 2018, U.S. Pat. No. 10,765,427, entitled METHOD FOR ARTICULATING A SURGICAL INSTRUMENT, which issued on Sep. 8, 2020, U.S. Pat. No. 11,291,445, entitled SURGICAL STAPLE CARTRIDGES WITH INTEGRAL AUTHENTICATION KEYS, which issued on Apr. 5, 2022, U.S. Pat. No. 8,864,007, entitled IMPLANTABLE FASTENER CARTRIDGE HAVING A NON-UNIFORM ARRANGEMENT, which issued on Oct. 21, 2014, U.S. Pat. No. 11,490,890, entitled COMPRESSIBLE NON-FIBROUS ADJUNCTS, which issued on Nov. 8, 2022, U.S. Pat. No. 10,952,724 entitled THREE DIMENSIONAL ADJUNCTS, which issued on Mar. 23, 2021, U.S. Pat. No.

9,770,245, entitled LAYER ARRANGEMENTS FOR SUR-GICAL STAPLE CARTRIDGES, which issued on Sep. 26, 2017, U.S. Pat. No. 10,123,798, entitled TISSUE THICK-NESS COMPENSATOR COMPRISING CONTROLLED RELEASE AND EXPANSION, which issued on Nov. 13, 2018, U.S. Pat. No. 10,166,023, entitled METHOD OF APPLYING A BUTTRESS TO A SURGICAL STAPLER END EFFECTOR, which issued on Jan. 1, 2019, U.S. Pat. No. 11,207,065, entitled METHOD FOR FABRICATING SURGICAL STAPLER ANVILS, which issued on Dec. 28, 2021, U.S. Pat. No. 8,141,762, entitled SURGICAL STA-PLER COMPRISING A STAPLE POCKET, which issued on Mar. 27, 2012, U.S. Pat. No. 8,876,857, entitled END EFFECTOR WITH REDUNDANT CLOSING MECHA-NISMS, which issued on Nov. 4, 2014, U.S. Pat. No. 9,629,631, entitled COMPOSITE DRIVE BEAM FOR SURGICAL STAPLING, which issued on Apr. 25, 2017, U.S. Patent Application Publication No. 2022/0346858, entitled METHOD FOR OPERATING A SURGICAL INSTRUMENT INCLUDING SEGMENTED ELEC-TRODES, which published on Nov. 3, 2022, U.S. Patent Application Publication No. 2022/0304680, entitled DRIV-ERS FOR FASTENER CARTRIDGE ASSEMBLIES HAV-ING ROTARY DRIVE SCREWS, which published on Sep. 29, 2022, U.S. Patent Application Publication No. 2022/0304679, entitled METHOD OF USING A POWERED STAPLING DEVICE, which published on Sep. 29, 2022, U.S. Patent Publication No. 2019/0298350, entitled METH-ODS FOR CONTROLLING A POWERED SURGICAL STAPLER THAT HAS SEPARATE ROTARY CLOSURE AND FIRING SYSTEMS, which published on Oct. 3, 2019, U.S. Patent Application Publication No. 2017/0367695, entitled STAPLE CARTRIDGE COMPRISING WIRE STAPLES AND STAMPED STAPLES, which published on Dec. 28, 2017, U.S. Patent Application Publication No. 2015/0134077, entitled SEALING MATERIALS FOR USE IN SURGICAL STAPLING, which published on May 14, 2015, U.S. Patent Application Publication No. 2018/0168615, entitled METHOD OF DEFORMING STAPLES FROM TWO DIFFERENT TYPES OF STAPLE CAR-TRIDGES WITH THE SAME SURGICAL STAPLING INSTRUMENT, which published on Jun. 21, 2018, U.S. Patent Application Publication No. 2018/0132849, entitled STAPLE FORMING POCKET CONFIGURATIONS FOR CIRCULAR SURGICAL STAPLER ANVIL, which pub-lished on May 17, 2018, U.S. Patent Application Publication No. 2018/0168613, entitled SURGICAL INSTRUMENTS WITH JAWS THAT ARE PIVOTABLE ABOUT A FIXED AXIS AND INCLUDE SEPARATE AND DISTINCT CLO-SURE AND FIRING SYSTEMS, which published on Jun. 21, 2018, U.S. Patent Application Publication No. 2017/0319205, entitled POWERED END EFFECTOR ASSEM-BLY WITH PIVOTABLE CHANNEL, which published on Nov. 9, 2017, U.S. Patent Application Publication No. 2014/0001231, entitled FIRING SYSTEM LOCKOUT ARRANGEMENTS FOR SURGICAL INSTRUMENTS, which published on Jan. 2, 2014, U.S. Patent Application Publication No. 2016/0095596, entitled APPARATUS FOR ENDOSCOPIC PROCEDURES, which published on Apr. 7, 2016, U.S. Patent Application Publication No. 2015/0297199, entitled ADAPTER ASSEMBLY WITH GIMBAL FOR INTERCONNECTING ELECTROMECHANICAL SURGICAL DEVICES AND SURGICAL LOADING UNITS, AND SURGICAL SYSTEMS THEREOF, which published on Oct. 22, 2015, U.S. Patent Application Publi-cation No. 2022/0031351, entitled SURGICAL INSTRU-MENTS WITH DIFFERENT ARTICULATION JOINT ARRANGEMENTS FOR ACCOMMODATING FLEX-IBLE ACTUATORS, which published on Feb. 3, 2022, U.S. Patent Application Publication No. 2022/0031320, entitled SURGICAL INSTRUMENTS WITH FLEXIBLE FIRING MEMBER ACTUATOR CONSTRAINT ARRANGE-MENTS, which published on Feb. 3, 2022, U.S. Patent Application Publication No. 2023/0119119, entitled CABLE-DRIVEN ACTUATION SYSTEM FOR ROBOTIC SURGICAL TOOL ATTACHMENT, which published on Apr. 20, 2023, International Patent Publication No. WO2018/071497, entitled STAPLER CARTRIDGE WITH AN INTEGRAL KNIFE, which published on Apr. 18, 2018, International Patent Publication No. WO2018/049211, entitled WRIST ARCHITECTURE, which pub-lished on Mar. 15, 2018, U.S. Pat. No. 11,298,129, entitled METHOD FOR PROVIDING AN AUTHENTICATION LOCKOUT IN A SURGICAL STAPLER WITH A REPLACEABLE CARTRIDGE, which issued on Apr. 12, 2022, U.S. Pat. No. 10,898,183, entitled ROBOTIC SUR-GICAL INSTRUMENT WITH CLOSED LOOP FEED-BACK TECHNIQUES FOR ADVANCEMENT OF CLO-SURE MEMBER DURING FIRING, which issued on Jan. 26, 2021, U.S. Pat. No. 5,485,947, entitled LINEAR STA-PLING MECHANISM WITH CUTTING MEANS, which issued on Jan. 23, 1996, International Patent Publication No. WO2018/049206, entitled STAPLER RELOAD DETEC-TION AND IDENTIFICATION, which published on Mar. 15, 2018, U.S. Patent Application Publication No. 2016/0249920, entitled Surgical fastener applying apparatus, which published on Sep. 1, 2016, U.S. Design Patent No. D974,560, entitled STAPLE CARTRIDGE, which issued on Jan. 3, 2023, U.S. Design Patent No. D967,421, entitled STAPLE CARTRIDGE, which issued on Oct. 18, 2022, U.S. Design Patent No. D933,220, entitled BUTTRESS ASSEMBLY FOR A SURGICAL STAPLER, which issued on Oct. 12, 2021, U.S. Pat. No. 9,839,420, entitled TISSUE THICKNESS COMPENSATOR COMPRISING AT LEAST ONE MEDICAMENT, which issued on Dec. 12, 2017, U.S. Pat. No. 10,588,623, entitled ADHESIVE FILM LAMINATE, which issued on Mar. 17, 2020, U.S. Pat. No. 8,499,992, entitled DEVICE AND METHOD FOR CON-TROLLING COMPRESSION OF TISSUE, which issued on Aug. 6, 2013, U.S. Patent Application Publication No. 2022/0378427, entitled STAPLING INSTRUMENT COM-PRISING JAW MOUNTS, which published on Dec. 1, 2022, U.S. Pat. No. 10,349,939, entitled METHOD OF APPLYING A BUTTRESS TO A SURGICAL STAPLER, which issued on Jul. 16, 2019, U.S. Pat. No. 9,386,988, entitled RETAINER ASSEMBLY INCLUDING A TISSUE THICKNESS COMPENSATOR, which issued on Jul. 12, 2016, U.S. Pat. No. 9,072,535, entitled SURGICAL STA-PLING INSTRUMENTS WITH ROTATABLE STAPLE DEPLOYMENT ARRANGEMENTS, which issued on Jul. 7, 2015, and U.S. Pat. No. 9,844,369, entitled, SURGICAL END EFFECTORS WITH FIRING ELEMENT MONI-TORING ARRANGEMENTS, which issued on Dec. 19, 2017 are incorporated by reference herein.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRU- MENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/235,972, entitled MOTORIZED SURGICAL INSTRUMENT, now U.S. Pat. No. 9,050,083.

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one or more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

It is worthy to note that any reference numbers included in the appended claims are used to reference exemplary embodiments/elements described in the present disclosure. Accordingly, any such reference numbers are not meant to limit the scope of the subject matter recited in the appended claims.

While this invention has been described as having exemplary designs, the present invention may be further modified within the spirit and scope of the disclosure. This application is therefore intended to cover any variations, uses, or adaptations of the invention using its general principles.

It is worthy to note that any reference numbers included in the appended claims are used to reference exemplary embodiments/elements described in the present disclosure. Accordingly, any such reference numbers are not meant to limit the scope of the subject matter recited in the appended claims.

What is claimed is:

1. A surgical stapling assembly, comprising:
a cartridge body, comprising:
a deck configured to support patient tissue, wherein the deck comprises a proximal end and a distal end;
a plurality of staple cavities defined in the deck;
a longitudinal slot defined in the deck, wherein the longitudinal slot extends from the proximal end toward the distal end, wherein the longitudinal slot defines a longitudinal axis, wherein the longitudinal slot is defined by an inner cartridge wall, wherein the staple cavities are arranged in longitudinal rows on opposite sides of the longitudinal slot, and wherein the longitudinal slot is configured to receive at least a portion of a firing driver during a firing stroke; and
an outer cartridge wall extending longitudinally between the proximal end and the distal end; and
a plurality of staples removably stored in the staple cavities;
a plurality of staple drivers; and
a sled movable longitudinally through the cartridge body from a proximal unfired position to a distal fired position by the firing driver to lift the staple drivers within the staple cavities to eject the staples from the staple cavities during the firing stroke;
wherein a portion of the sled is positioned under the inner cartridge wall at a cross section taken at a plane perpendicular to the longitudinal axis, wherein the inner cartridge wall comprises a first lateral pillar width and a first pillar height in the plane, wherein the first lateral pillar width comprises a first average lateral width of the inner cartridge wall along the first pillar height, wherein the outer cartridge wall comprises a second lateral pillar width and a second pillar height in the support plane, wherein the second lateral pillar width comprises a second average lateral width of the outer cartridge wall along the second pillar height, and wherein the first average lateral width is wider than the second average lateral width.

2. The surgical stapling assembly of claim 1, wherein the sled is engaged with the inner cartridge wall in the plane.

3. The surgical stapling assembly of claim 1, wherein the cross section is taken perpendicular to the longitudinal axis at the proximal unfired position of the sled.

4. The surgical stapling assembly of claim 1, wherein the cartridge body further comprises an intermediate cartridge wall situated laterally between the inner cartridge wall and the outer cartridge wall, and wherein the intermediate cartridge wall comprises a third lateral pillar width and a third pillar height in the support plane, wherein the third lateral pillar width comprises a third average lateral width of the intermediate cartridge wall along the third pillar height, and wherein the third average lateral width is narrower than the first average lateral width and wider than the second average lateral width.

5. The surgical stapling assembly of claim 1, further comprising a support insert positioned within the longitudinal slot.

6. The surgical stapling assembly of claim 5, wherein the support insert comprises a material different than the cartridge body.

7. The surgical stapling assembly of claim 5, wherein the sled comprises a base comprising an upper surface that faces the deck, and wherein the upper surface of the base is configured to engage the bottom surface of the support insert during the firing stroke.

8. The surgical stapling assembly of claim 5, wherein the cartridge body further comprises a ledge extending laterally into the longitudinal slot, wherein the support insert is positioned against the ledge.

9. The surgical stapling assembly of claim 5, wherein the support insert comprises a ridge extending longitudinally along a length of the support insert, wherein the ridge extends inwardly into the longitudinal slot, and wherein the sled comprises:
a base;
a plurality of ramped wedges extending from the base; and
a central rib extending from the base that is configured to be received within the longitudinal slot, wherein the central rib is configured to engage the ridge of the support insert during the firing stroke.

10. The surgical stapling assembly of claim 5, wherein an insert slot is defined in a longitudinal length of the support insert, and wherein the sled comprises:
a base;
a plurality of ramped wedges extending from the base; and
a central rib extending from the base and configured to be received within the insert slot, wherein the central rib comprises a projection configured to engage the insert slot during the firing stroke.

11. The surgical stapling assembly of claim 1, wherein each staple driver comprises:
a first driver column configured to support a first staple of the plurality of staples within a first staple cavity of the plurality of staple cavities, wherein the first driver column comprises a first distal end and a first proximal end;
a second driver column configured to support a second staple of the plurality of staples within a second staple cavity of the plurality of staple cavities, wherein the second driver column comprises a second distal end and a second proximal end; and
a third driver column configured to support a third staple of the plurality of staples within a third staple cavity of the plurality of staple cavities, wherein the third driver column comprises a third distal end and a third proximal end, wherein the third driver column is positioned between the first driver column and the second driver column, wherein the second proximal end is distal to the first proximal end and the second proximal end, and wherein the first distal end and the third distal end are configured to engage the cartridge body as the staple driver is lifted from an unfired position to a fired position and a clearance is defined between the first proximal end and the cartridge body and the third proximal end and the cartridge body as the staple driver is lifted from the unfired position to the fired position.

12. The surgical stapling assembly of claim 11, wherein the clearance comprises a first clearance, and wherein a second clearance is defined between the second distal end and the cartridge body as the staple driver is lifted from the unfired position to the fired position.

13. The surgical stapling assembly of claim 11, wherein the cartridge body is configured to counteract longitudinal rotation of the staple driver proximal end over distal end through engagement between the second proximal end and the cartridge body.

14. The surgical stapling assembly of claim 1, further comprising a pan attached to the cartridge body, wherein the cartridge body comprises a bottom opposite the deck, and wherein the pan is configured to prevent the staple drivers and the sled from falling out of the bottom of the cartridge body.

15. A surgical staple cartridge, comprising:

a cartridge body, comprising:

a deck configured to support patient tissue, wherein the deck comprises a proximal end and a distal end;

a plurality of staple cavities defined in the deck;

a longitudinal slot defined in the deck, wherein the longitudinal slot extends from the proximal end toward the distal end, wherein the longitudinal slot defines a longitudinal axis, wherein the longitudinal slot is defined by an inner wall, wherein the staple cavities are arranged in longitudinal rows on opposite sides of the longitudinal slot, and wherein the longitudinal slot is configured to receive at least a portion of a firing driver during a firing stroke; and an outer wall extending longitudinally between the proximal end and the distal end; and a plurality of staples removably stored in the staple cavities; and a ramp movable longitudinally through the cartridge body from a proximal unfired position to a distal fired position by the firing driver to eject the staples from the staple cavities during the firing stroke;

wherein a portion of the sled is positioned under the inner wall at a cross section taken at a plane perpendicular to the longitudinal axis, wherein the inner wall comprises a first average lateral pillar width and a first pillar height in the plane, wherein the outer wall comprises a second average lateral pillar width and a second pillar height in the plane, and wherein the first average lateral pillar width is wider than the second average lateral pillar width.

16. A surgical staple cartridge, comprising:

a cartridge body, comprising:

a tissue-supporting surface configured to support patient tissue, wherein the tissue-supporting surface comprises a proximal end and a distal end;

a plurality of staple cavities defined in the tissue-supporting surface;

an inner lateral cartridge wall;

an outer lateral cartridge wall; and a longitudinal slot defined in the tissue-supporting surface, wherein the longitudinal slot extends from the proximal end toward the distal end, wherein the longitudinal slot defines a longitudinal axis, wherein the longitudinal slot is defined by the inner lateral cartridge wall, wherein the staple cavities are arranged in longitudinal rows on opposite sides of the longitudinal slot, and wherein the longitudinal slot is configured to receive at least a portion of a firing driver during a firing stroke;

a plurality of staples removably stored in the staple cavities; and a sled movable longitudinally through the cartridge body from a proximal unfired position to a distal fired position by the firing driver to eject the staples from the staple cavities during the firing stroke; wherein the inner lateral cartridge wall comprises a first average width at a cross section taken at a plane perpendicular to the longitudinal axis, wherein the outer lateral cartridge wall comprises a second average width in the plane, and wherein the first average width is greater than the second average width.

17. The surgical staple cartridge of claim 16, further comprising a support insert positioned within the longitudinal slot, wherein the support insert comprises a material different than the cartridge body, wherein the support insert comprises a bottom configured to engage a cartridge channel of a stapling end effector within which the surgical staple cartridge is configured to be installed.

18. The surgical staple cartridge of claim 17, wherein the sled is configured to engage the support insert during the firing stroke to resist deflection of the cartridge body.

* * * * *